US011754569B2

(12) United States Patent
Liu et al.

(10) Patent No.: US 11,754,569 B2
(45) Date of Patent: Sep. 12, 2023

(54) METHODS FOR CHARACTERIZING PROTEIN COMPLEXES

(71) Applicant: Regeneron Pharmaceuticals, Inc., Tarrytown, NY (US)

(72) Inventors: Nina Liu, Chappaqua, NY (US); Michael Rosconi, New City, NY (US); Erica Pyles, New City, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 196 days.

(21) Appl. No.: 16/553,312

(22) Filed: Aug. 28, 2019

(65) Prior Publication Data
US 2020/0072844 A1 Mar. 5, 2020

Related U.S. Application Data

(60) Provisional application No. 62/724,700, filed on Aug. 30, 2018.

(51) Int. Cl.
*G01N 33/68* (2006.01)
*G01N 21/49* (2006.01)
(52) U.S. Cl.
CPC ......... *G01N 33/6845* (2013.01); *G01N 21/49* (2013.01)
(58) Field of Classification Search
CPC .... G01N 21/47; G01N 21/49; G01N 30/0005; G01N 33/6803; G01N 33/6845
See application file for complete search history.

(56) References Cited

U.S. PATENT DOCUMENTS

2015/0110818 A1 4/2015 Matthias et al.
2019/0177436 A1* 6/2019 Devalaraja-Narashimha ............... C07K 16/44

FOREIGN PATENT DOCUMENTS

WO 2011/121560 A2 10/2011
WO 2017/129737 A1 8/2017

OTHER PUBLICATIONS

Favuzza et al., "Structure of the malaria vaccine candidate antigen CyRPA and its complex with a parasite invasion inhibitory antibody," eLife, 2017; 6: e20383, pp. 1-21.*
Mack et al., "A small bispecific antibody construct expressed as a functional single-chain molecule with high tumor cell cytotoxicity," PNAS, 1995, vol. 92, No. 15, pp. 7021-7025.*
Printout retrieved from https://www.bosterbio.com/anti-protein-z-antibody-a06491-boster.html on Aug. 11, 2021.*
Wang et al., "Monoclonal antibody pharmacokinetics and pharmacodynamics," Clin. Pharmacol. Ther., 2008, vol. 84, No. 5, pp. 548-558.*

Litzén et al., "Separation and quantitation of monoclonal antibody aggregates by asymmetrical flow field-flow fractionation and comparison to gel permeation chromatography," Anal. Biochem., 1993, vol. 212, No. 2, pp. 469-480.*
Wu et al., "Molecular characterization of branched polysaccharides from Tremella fuciformis by asymmetrical flow field-flow fractionation and size exclusion chromatography," J. Sep. Sci., 2017, vol. 40, issue 21, pp. 4272-4280.*
Rebolj et al., "Characterization of a Protein Conjugate Using an Asymmetrical-Flow Field-Flow Fractionation and a Size-Exclusion Chromatography with Multi-Detection System," Anal. Chem., 2012, vol. 84, No. 17, pp. 7374-7383.*
Mahler, et al., "Protein aggregation: Pathways, induction factors and analysis," Journal of Pharmaceutical Sciences, 98(9):2909-2934 (2009).
Matthews, David, "Developability assessment of therapeutic antibodies," https://www.drugtargetreview.com/article/32916/developability-assessment-of-therapeutic-antibodies/ (2017).
Moharana, Kedar, et al., "Structural and Mechanistic Paradigm of Leptin Receptor Activation Revealed by Complexes with Wild-Type and Antagonist Leptins," Structure, 22(6):866-877 (2014).
The International Search Report and Written Opinion of the International Searching Authority, dated Nov. 22, 2019 (14 pages).
Bria, C.R.M., "Development Of Asymmetrical Flow Field-Flow Fractionation For The Characterization Of Proteins. Protein Aggregation, And Nanoparticles," Doctoral Thesis for Colorado School of Mines (2016).
Bria, C.R.M., et al., "Probing Submicron Aggregation Kinetics of an IgG Protein by Asymmetrical Flow Field-Flow Fractionation", J Pharm Sci, 105:31-39 (2016).
Brusotti G., et al., "Advances on Size Exclusion Chromatography and Applications on the Analysis of Protein Biopharmaceuticals and Protein Aggregates: A Mini Review" Chromatographia, 81:3-23 (2018).
Davda, J.P. et al., "Properties of a general PK/PD model of antibody-ligand interactions for therapeutic antibodies that bind to soluble endogenous targets," mAbs, 2(5):576-588 (2010).
Fraunhofer, W. and Winter, G., "The use of asymmetrical flow field-flow fractionation in pharmaceutics and biopharmaceutics," Eur. J. Pharm. Biopharm, 58:369-383 (2004).
Harder, M.J., et al., "Incomplete inhibition by eculizumab: mechanistic evidence for residual C5 activity during strong complement activation," Blood, 129(8):970-980 (2017).
Kendrick BS, Kerwin BA, Chang BS, Philo JS. (2001). Anal Biochem. 299(2), 136-46. "Online Size-Exclusion High-Performance Liquid Chromatography Light Scattering and Differential Refractometry Methods to Determine Degree of Polymer Conjugation to Proteins and Protein-Protein or Protein-Ligand Association States".
Pollastrini, J., et al., "Field flow fractionation for assessing neonatal Fc receptor and Fcγ receptor binding to monoclonal antibodies in solution," Analytical Biochemistry, 414:88-98 (2011).
Messaud F.A., et al., "An overview on field-flow fractionation techniques and their applications in the separation and characterization of polymers," Progress in Polymer science (2009).

(Continued)

*Primary Examiner* — Galina M. Yakovleva
(74) *Attorney, Agent, or Firm* — McCarter & English, LLP

(57) ABSTRACT

Methods for characterizing protein complexes formed between protein drug products and soluble ligands are provided herein. The disclosed methods can determine the size, heterogeneity, and conformation of protein complexes.

20 Claims, 23 Drawing Sheets

(56) References Cited

OTHER PUBLICATIONS

Ryman, J.T. and B. Meibohm, "Pharmacokinetics of Monoclonal Antibodies," CRT Pharmacometrics Syst Pharmacol, 6:576-588 (2017).
St. Clair JB, Wysocki LJ, et.al. (2017) "Immunogenicity of Isogenic IgG in Aggregates and Immune Complexes". PLoS One 12(1): e0170556. doi:10.1371/journal.pone.017055.
Wahlund, Karl-Gustav, "Flow field-flow fractionation: Critical Overview," Journal of Chromatography A, 1287:97-112 (2013).
Wolken DMA, Economides AN, et.al. (2018) "The obligatory role of Activin A in the formation of heterotopic bone in Fibrodysplasia Ossificans Progressiva". Bone 109, 210-217.
Wyatt, PJ. (1993) Anal. Chim. Acta 272(1), 1-40, "Light Scattering and the Absolute Characterization of Macromolecules".
Zhou, M., et al., "Current Experimental Methods for Characterizing Protein-Protein Interactions," Chem Med Chem, 11:738-756 (2016).
International Preliminary Report on Patentability received for PCT Patent Application No. PCT/US19/48526, dated Mar. 11, 2021, 9 pages.

\* cited by examiner

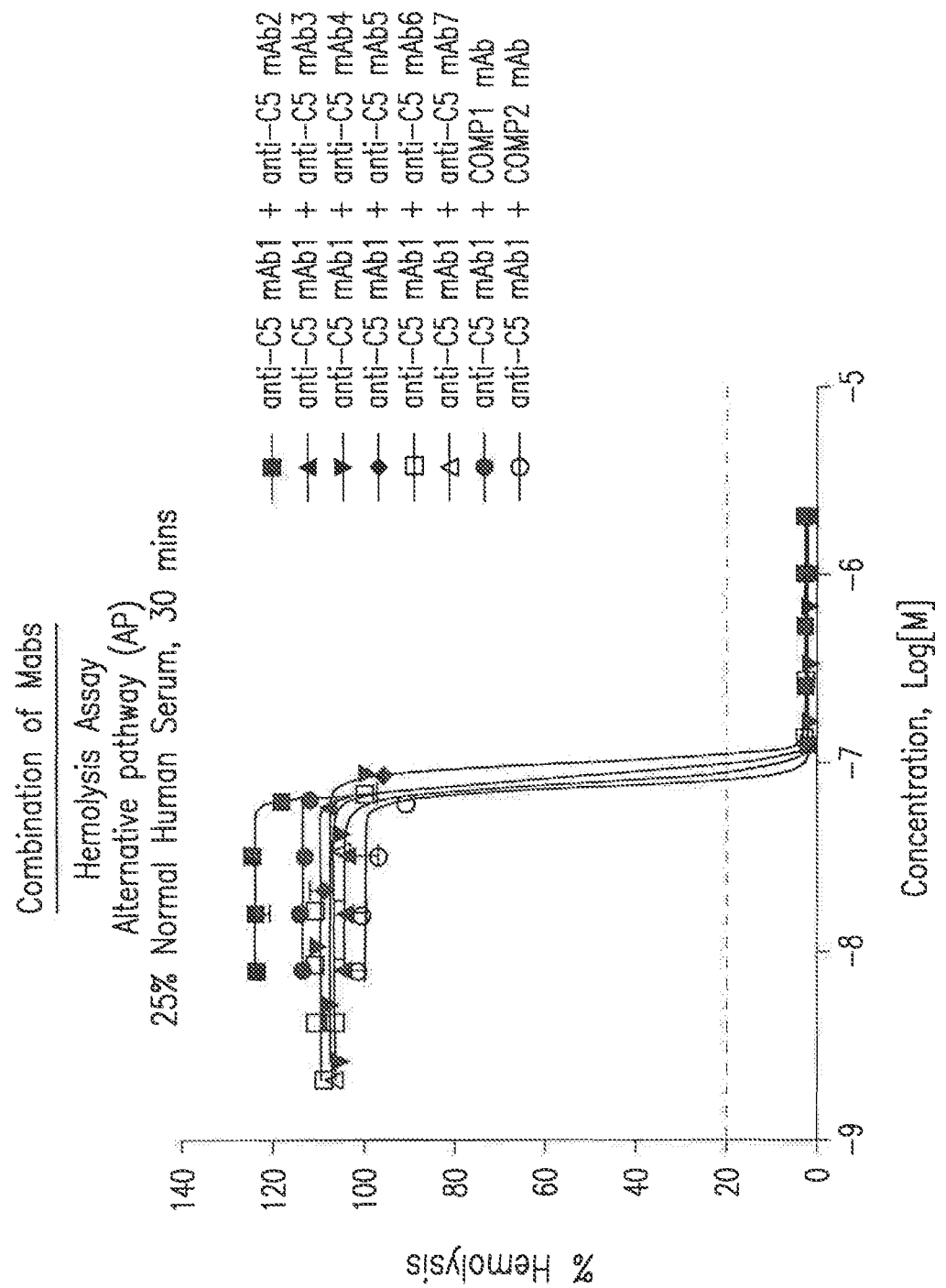

METHODS FOR CHARACTERIZING PROTEIN COMPLEXES

CROSS-REFERENCE TO RELATED APPLICATIONS

This application claims benefit of and priority to U.S. Provisional Patent Application No. 62/724,700 file on Aug. 30, 2018, which is incorporated by reference in its entirety.

TECHNICAL FIELD OF THE INVENTION

This invention is generally related to systems and methods of characterizing protein complexes.

BACKGROUND OF THE INVENTION

Monoclonal antibodies (mAbs) are a growing therapeutic field, with over 50 monoclonal antibodies currently on the market. Combination therapy of more than one monoclonal antibody has the potential to improve the efficacy of existing monotherapies. Certain soluble substances, particularly multimeric substances with several repeated epitopes, may bind with two or more antibodies, leading to the formation of large complexes. The production of large, heterogeneous antibody complexes is referred to as "paper-dolling". Large complexes of antibodies can be rapidly eliminated by phagocytosis, leading to reduced efficacy of the antibody. Large protein complexes can also increase immunogenicity of the mAb.

Protein complexes can range in size from nanometer to visible particles making their characterization by a single analytical technique difficult. One of the most widespread techniques used to determine the size of particles from ~1 nm to ~1 μm is dynamic light scattering (DLS). DLS is an analytical technique used to determine protein size distribution profile, and is amenable to high throughput applications (Zhou, M., et al., *Chem Med Chem*, 11:738-756 (2016)). The Brownian motion of proteins in solution causes light to be scattered, with the resultant scattered intensity fluctuations dependent on particle size. Thus, average radius and the width of the distribution in terms of polydispersity can be determined. However, DLS results are often biased towards larger particles and the particle populations must differ by a factor of at least three to be resolved. Therefore, DLS alone is not sufficient for analyzing protein complexes.

The high polydispersity of many aggregate samples require separation-based methods to provide more detailed information due to the wide size range of protein complexes. Size exclusion chromatography (SEC) is currently the most commonly used chromatographic technique for protein separation (Brusotti, et al., *Chromatogrophia*, 81:3-23 (2018)). In SEC, separation occurs according to hydrodynamic volume or size of molecules. Smaller molecules are retained longer because they are able to diffuse into the pores of the stationary phase, while larger molecules elute first because they are excluded from the pores. However, SEC is limited by upper molecular weight exclusion limits, sample adsorption to the stationary phase, shear degradation at high pressures and flow rates, and an inability to separate analytes based on composition.

Flow field-flow fractionation (FFF) is a promising alternative to SEC when it comes to separation of large proteins and high molar mass polymers. FFF sample separation uses a flow-assisted separation and fractionation method in which the analytes are separated along a ribbon like channel by differences in their diffusion coefficients (Fraunhofer, W. and Winter, G., *Eur. J. Pharm. Biopharm*, 58:369-383 (2004)). FFF can separate analytes in a wide size range (from nanometers to microns). The open channel of FFF renders reduced sample loss, low pressures, and low shear rates. While FFF has been used in combination with other molecular techniques such as light scattering to detect protein aggregates, there is still a growing need to more fully characterize heterogeneity and conformation of protein complexes, including mAb and soluble ligand complexes.

Therefore, it is an object of the invention to provide methods for identifying protein drug products that have the ability to form large protein complexes.

It is another object of the invention to provide methods of identifying and characterizing protein drug product and soluble ligand complexes.

SUMMARY OF THE INVENTION

Methods for characterizing protein complexes in a sample are provided. One embodiment provides a method for assessing the stoichiometry and size distribution of protein complexes in a sample by fractionating the sample by asymmetrical flow field flow fractionation (A4F), and determining the stoichiometry and size distribution of the protein complexes in the sample using Multi-Angle Laser Light Scattering (MALLS). In some embodiments, the protein complexes contain an antibody or fusion protein bound to its ligand. The ligand is typically a soluble ligand. The ligand can be monomeric or multimeric. In one embodiment the ligand can be a homodimer or heterodimer. In another embodiment the protein complexes comprise or consist of antibody:ligand complexes or fusion protein:ligand complexes.

Another embodiment provides a method for selecting a lead protein drug product by adding a first protein drug product to a first sample containing a target or ligand of the first protein drug product to produce protein:ligand complexes, and adding a second protein drug product to a second sample containing the target or ligand to form protein:ligand complexes. The method includes separating the protein:ligand complexes and determining the molar mass, stoichiometry, and size distribution of protein:ligand complexes using asymmetrical flow field flow fractionation—MALLS. The method also includes selecting the protein drug product that forms fewer large protein:ligand complexes as the lead target protein drug. Typically, the protein drug product is an antibody or antigen binding fragment thereof, a fusion protein, or a recombinant protein. In some embodiments, the ligand is a soluble ligand. The ligand can be monomeric or multimeric. In some embodiments the large protein complexes are heterometric.

Another embodiment provides a pharmaceutical composition containing the lead protein drug product selected using the method described above.

In some embodiments, the disclosed methods can be used to determine if two individual antibodies targeting the same ligand will form large, heterogeneous complexes.

Still another embodiment provides a method for characterizing protein complexes formed between protein drug products and soluble ligands by preparing a sample containing the protein drug product and its ligand to product protein drug product ligand complexes. The method include fractionating the protein drug:ligand complexes and analyzing the fractionated protein drug:ligand complexes by multi-angle laser light scattering to determine the size and heterogeneity of protein complexes. In one embodiment, fractionating the total protein is performed by asymmetrical flow field flow fractionation. The concentration of the protein can be determined with an additional step of UV/Vis.

The differences in conformation of protein complexes formed by different protein drug products to the same ligand can be determined by comparing the elution profile/time of protein drug product:ligand complexes formed by the different protein drug products. Different elution profiles/times of complexes with the same molar mass indicate that the complexes may have different conformations or shapes. In one embodiment, each protein drug product and the same soluble ligand is analyzed separately in order to calculate a theoretical molar mass for each individual component, wherein the theoretical molar mass is used to determine the heterogeneity of each protein complex.

Another embodiment provides a method for characterizing protein complexes formed between protein drug products and soluble ligands by fractionating protein drug product:ligand complexes using asymmetrical flow-field flow fractionation, analyzing the fractionated protein drug product:ligand complexes by multi-angle laser light scattering to Characterize the size, stoichiometry, or both of protein drug:ligand complexes, and determining the heterogeneity of the protein complexes by comparing the size of each protein complex to the theoretical size of each individual component to determine the components that make up each complex.

BRIEF DESCRIPTION OF THE DRAWINGS

FIGS. 6A and 6B are line graphs showing percent hemolysis of rabbit red blood cells with increasing concentrations of various anti-Protein Z mAbs (FIG. 6A) or combinations of Ab3 and various anti-Protein Z mAbs (FIG. 6B). The X axis represents concentration of mAb (Log [M]). The Y axis represents percent hemolysis.

DETAILED DESCRIPTION OF THE INVENTION

I. Definitions

Figure 1A:
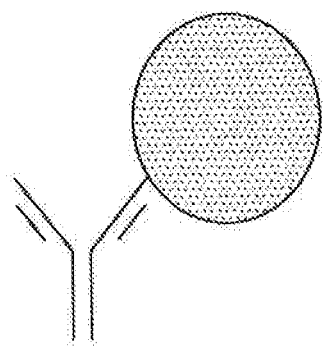
FIG. 1A is an illustration of a complex formed between one antibody and one ligand.

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

"Protein" refers to a molecule comprising two or more amino acid residues joined to each other by a peptide bond. Protein includes polypeptides and peptides and may also include modifications such as glycosylation, lipid attachment, sulfation, gamma-carboxylation of glutamic acid residues, alkylation, hydroxylation and ADP-ribosylation. Proteins can be of scientific or commercial interest, including protein-based drugs, and proteins include, among other things, enzymes, ligands, receptors, antibodies and chimeric or fusion proteins. Proteins are produced by various types of recombinant cells using well-known cell culture methods, and are generally introduced into the cell by genetic engineering techniques (e.g., such as a sequence encoding a chimeric protein, or a codon-optimized sequence, an intronless sequence, etc.) where it may reside as an episome or be intergrated into the genome of the cell.

"Antibody" refers to an immunoglobulin molecule consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. The term antibody also includes bispecific antibody, which includes a heterotetrameric immunoglobulin that can bind to more than one different epitope. Bispecific antibodies are generally described in U.S. Pat. No. 8,586,713, which is incorporated by reference into this application.

"Fc fusion proteins" comprise part or all of two or more proteins, one of which is an Fc portion of an immunoglobulin molecule, which are not otherwise found together in nature. Preparation of fusion proteins comprising certain heterologous polypeptides fused to various portions of antibody-derived polypeptides (including the Fc domain) has been described, e.g., by Ashkenazi et al., Proc. Natl. Acad. ScL USA 88: 10535, 1991; Byrn et al., Nature 344:677, 1990; and Hollenbaugh et al., "Construction of Immunoglobulin Fusion Proteins", in Current Protocols in Immunology, Suppl. 4, pages 10.19.1-10.19.11, 1992. "Receptor Fc fusion proteins" comprise one or more extracellular domain(s) of a receptor coupled to an Fc moiety, which in some embodiments comprises a hinge region followed by a CH2 and CH3 domain of an immunoglobulin. In some embodiments, the Fe-fusion protein comprises two or more distinct receptor chains that bind to a one or more ligand(s). For example, an Fc-fasion protein is a trap, such as for example an IL-1 trap or VEGF trap.

As used herein, "soluble ligand" refers to polar or charged ligands that cannot readily cross the plasma membrane of a cell. Most soluble ligands bind to the extracellular domains of cell-surface receptors.

"A4F" represents asymmetrical flow field-flow fractionation which is a fractionating technique in which separation of analytes is achieved through the interaction of the sample with an external, perpendicular physical field.

Multi angle light scattering (MALS) describes a technique for measuring the light scattered by a sample into a plurality of angles. It is used for determining both the absolute molar mass and the average size of molecules in solution, by detecting how they scatter light. Collimated light from a laser source is most often used, in which case the technique can be referred to as multi angle laser light scattering (MALLS). In practice the terms MALS and MALLS are used interchangeably.

As used herein, "Brownian motion" refers to the continuous motion of particles suspended in liquid.

II. Methods For Characterizing Protein Complexes

Monoclonal antibody combination therapy has emerged as a promising therapeutic strategy for diseases such as cancer and inflammatory conditions in which multiple signaling pathways are involved. In addition, administration of more than one monoclonal antibody targeting the same pathway could be beneficial to completely block pathways involved in the pathogenesis of diseases when monotherapy alone does not fully inhibit the pathway. However, binding of therapeutic mAbs to soluble, multimeric targets can lead to the formation of large heterogeneous complexes. The size, shape, and conformation of a protein complex can affect immunogenicity and antibody clearance time, among other factors. Analysis of protein complexes is important to provide insight into the pharmacokinetics of a mAb during drug development.

Therefore, methods and systems for characterizing protein complexes are provided. One embodiment provides a method for assessing the stoichiometry and size distribution of heterogeneous protein drug product ligand complexes in a sample by fractionating the sample using asymmetrical flow field flow fractionation and determining the molar mass, stoichiometry, and size distribution of heterogeneous protein complexes in the sample using multi-angle laser light scattering. The protein complexes typically are comprised of a protein that specifically binds to a protein of interest also referred to as a target or ligand. In one embodiment the protein that specifically binds to the target is an antibody or fusion protein.

When an antibody or fusion protein is combined with its target or ligand in vivo or in vitro, a heterogeneous mixture of antibody:ligand or fusion protein:ligand can form. In one embodiment, binding of therapeutic proteins such as monoclonal antibodies (mAbs) or fusion proteins to soluble, multimeric targets lead to large heterogeneous complexes or large heteromeric complexes. For example, the large protein complexes can be characterized as a protein complex with a protein:ligand ratio selected from the group consisting of 3:2, 2:3, 4:4, 6:6, or $[2:2]_n$. Large heterogeneous complexes refer to complexes formed between multiple multimeric ligand molecules and multiple protein drug product molecules. The term large heteromeric complex refers to ligand bound by two different protein drug products, for example two different antibodies, two different fusion proteins, or an antibody and a fusion protein binding the same ligand at different sites.

Another embodiment provides a method of identifying protein drug products that form large heterogeneous complexes with soluble targets in vivo, in vitro, or both. The method includes preparing a sample containing a protein drug product and its soluble ligand to produce protein drug product:ligand complexes, fractionating the sample to separate the protein drug product:ligand complexes and analyzing the fractionated protein drug product:ligand complexes by multi-angle laser light scattering to determine the size and heterogeneity of protein complexes. In one embodiment, the protein sample is fractionated using asymmetrical flow field-flow fractionation.

Further details of the disclosed methods and systems are provided below.

A. System for Characterizing Protein Complexes

In one embodiment, the system includes an asymmetrical flow field-flow fractionation (A4F) system and a multi-angle laser light scattering (MALLS) system. An example of a commercially available A4F system is an Eclipse™ 3+ A4F Separation System. An example of a commercially available MALLS system is the Wyatt Technology Dawn HELEOS® II laser light scattering instrument. The system typically includes a UV/VIS detector and/or a refractive index detector. An exemplary commercially available UV/VIS detector is Agilent 1260 infinity UV detector. An exemplary commercially available refractive index detector is Optilab® T-rEX refractive index detector. In one embodiment the A4F system includes an A4F short channel fitted with a 350 W spacer and a 4 kDa MWCO NADIR® hydrophilic PES (PESH) membrane. In another embodiment, the A4F short channel is fitted with a 490 W spacer and a 10 kDa MWCO Nadir® regenerated cellulose membrane. Exemplary mobile phases include 10 mM phosphate and 500 mM NaCl at pH 7.0. However, an advantage of A4F over column chromatography separation is that there are no limitations on the type of mobile phase, or carrier fluid that can be used. In one embodiment, the samples are separated using a linear gradient over 60 minutes. In one embodiment, the channel flow and cross-flow program are specifically optimized to achieve a desired resolution on a case-by-case basis. It is to be understood that a person of skill in the art could modify and optimize the elution profile according to the resolution being required of the specific sample being separated using A4F.

Typically, the sample is injected into the sample inlet port of the A4F channel. The sample is then focused by allowing the carrier fluid to flow into the channel from both the inlet and outlet ports, meeting at a point in the channel, typically near the sample inlet port, to form a focusing zone. During the focusing period, particles from the injected sample are held in this focusing zone to allow for, relaxation prior to fractionation. The final step is fractionation of the particles. As particles flow along the channel, the perpendicularly-opposed cross-flow separation field pushes the molecules towards the bottom of the channel. As they accumulate near the bottom of the channel, they undergo a counter acting diffusion back into the channel against the cross-flow field. The extent to which the molecules can diffuse back into the channel is dictated by their natural Brownian motion, a characteristic defined by the translational diffusion coefficient, which, in turn, is related to the size and shape unique to each individual species. Generally, smaller particles have a faster diffusion coefficient than larger ones and are able to diffuse higher into the channel against the cross-flow field. The rate of laminar flow within the channel is not uniform, it travels in a parabolic pattern with the speed of the flow increasing towards the center of the channel and decreasing towards the upper and lower walls of the channel. Therefore, the rate at which particles will be carried through will depend on their position within the channel. Those with faster diffusion, located near the center of the channel, will be transported with a greater velocity. The larger particles in the shallow, slower moving stream near the bottom accumulation wall of the channel are transported with lower flow velocity and elute later than smaller particles. This results in a gentle separation of particles based on mass with the elution order of smallest to largest.

As the sample is flowing through the A4F channel, the leading portion of sample exits the channel through an outlet port. The multi-angle laser light scattering (MALLS) detector is in fluid communication with the A4F system and receives sample from the A4F outlet port. In some embodiments, the sample first flows through a UV/VIS detector to measure sample concentration as a function of absorbance. The MALLS system focuses a beam of polarized light (or a laser) onto the sample molecule and the scattered light is detected with a photo detector.

Multi angle light scattering (MALS) measures light being scattered from a sample containing molecules, particles, or protein complexes. This scattering depends on the optical configuration of the setup, and in a typical experimental realization, the light is then detected at one or several different angles. In the one-scattering-angle solution, the three most popular designs are 90 degrees (also right angle light scattering or RALS), 7 degrees (also low angle light scattering or LALS), or 173 degrees (also non-invasive back scattering or NIBS). In the multi-angle setup there are in principle those where the angles are fixed (this is most often called the MALS or MALLS setup) and those where the angles are variable (typically referred to as a light scattering goniometer or spectrometer). MALS usually refers to a system with multiple fixed angles used as part of a particle separation setup, for example A4F. The most widespread application MALS is as an absolute molar mass detector in conjunction with a concentration detector (like RI or single-wavelength UV).

MALS can be used to measure: $M_w$—weight-averaged molar mass of a protein complex; $R_g$—average radius of protein complex; and $A_2$—solubility of protein in solution.

B. Methods of Characterizing Protein Complexes

The disclosed systems and methods can be used to characterize protein complexes, for example protein drug product:ligand complexes in a sample. One embodiment provides a method for assessing the stoichiometry and size distribution of heterogeneous protein complexes in a sample by fractionating the sample by asymmetrical flow field flow fractionation (A4F), and determining the molar mass, stoichiometry and size distribution of protein complexes in the sample using Multi-Angle Laser Light Scattering (MALLS), wherein the complexes comprise or consist of antibody:ligand complexes or fusion protein:ligand complexes. In some embodiments, the ligand is a soluble ligand. Typically, the antibody is a monoclonal antibody. In one embodiment, the protein complex is characterized by its antibody or fusion protein to ligand ratio. In a non-limiting example, the antibody or fusion protein to ligand ratio can be selected from the group consisting of 1:0, 0:1, 1:1, 1:2, 2:1, 2:2, 3:2, 2:3, 4:4, 6:6, or $[2:2]_n$. It is to be understood that the antibody or fusion protein to ligand ratio will be dependent on the specific antibody or fusion protein and ligand that are being tested.

1. Mixtures of Protein Complexes

To determine the characteristics of protein complexes, a theoretical mass can be determined for each component of the complex. In one embodiment, each protein and ligand is the mixture is analyzed separately to determine a theoretical molar mass for each component. In one embodiment, a protein drug product and its ligand are mixed to form protein drug product:ligand complexes and the complexes are then characterized. The fractionated protein drug product:ligands are subjected to A4F-MALLS to determine molar mass of the complexes. The masses of the complexes are then compared to the theoretical molar mass of the individual components to determine the likely stoichiometric ratio of individual components present in each complex. In one embodiment, the methods can detect a 1:1 protein drug product:ligand complex In another embodiment, the methods can detect any ratio of protein drug product:ligand. In a non-limiting example, the methods can detect a protein drug product:ligand complex of 1:0, 0:1, 2:1, 1:2, 2:2, 3:2, 2:3, 4:4, 6:6, or $[2:2]_n$. It is to be understood that the antibody or fusion protein to ligand ratio will be dependent on the specific antibody or fusion protein and ligand that are being tested. In some embodiments, the complex contains multiple different protein drug products complexed with a common soluble ligand.

a. Ligands

The ligand in the protein drug product:ligand complex can be a monomeric or multimeric ligand. In one embodiment, the ligand is a soluble ligand. In some embodiments the soluble ligands correspond to the extracellular portions of transmembrane proteins including but not limited to transmembrane receptor proteins.

Figure 1B:
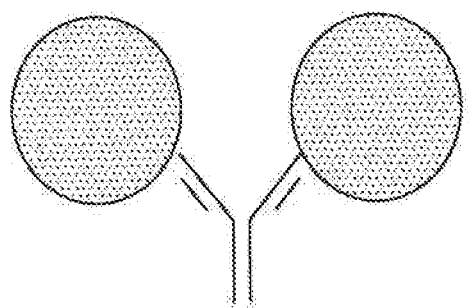
FIG. 1B is an illustration of a complex formed between one antibody and two ligands.
Figure 1C:
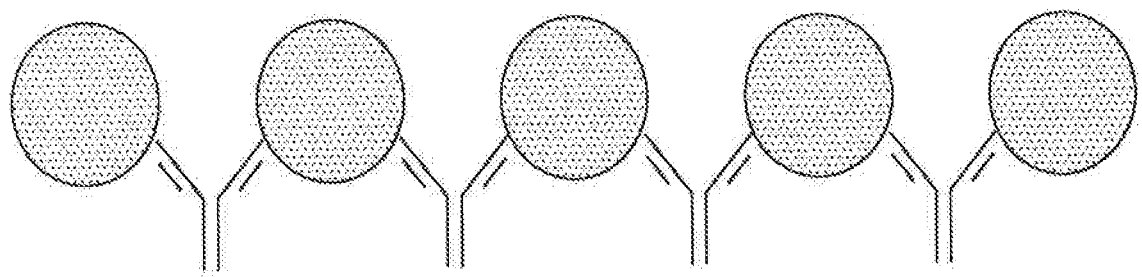
FIG. 1C is an illustration of a complex formed between four antibodies and five ligands, representative of "paper dolling".

Monomeric ligands contain only one protein or one protein unit. Multimeric ligands can be for example dimeric, trimeric, etc., containing multiple proteins or protein subunits. For example the ligands can be homodimer or heterodimers. In some embodiments, the multimeric ligands bind to more than one molecule of a protein drug product. FIG. 1A shows an exemplary 1:1 antibody:ligand complex. FIG. 1B shows an exemplary 1:2 antibody:ligand complex, and FIG. 1C shows an example of the "paper dolling" effect wherein each arm of an interior antibody binds to a different ligand creating a large, heterogeneous complex.

In one embodiment, the large, heterogeneous protein drug product:ligand complex has a size of 500 kDa or greater. In another embodiment, the heterogeneous protein drug product:ligand complex has a size of 500-4000 kDa. In another embodiment, the large, heterogeneous protein drug product:ligand has a ratio of protein drug product:ligand of 3:2, 2:3, 4:4, or 6:6.

In one embodiment, the disclosed methods are used to determine if a lead protein drug product designed to target a multimeric ligand will form large, heterogeneous protein drug product:ligand complexes.

In one embodiment, the disclosed methods can be used to determine if a multimeric ligand will form complexes with more than one protein drug product or fusion protein. The complexes that can be formed include but are not limited to protein:ligand ratios of 1:0, 0:1, 2:1, 1:2, 2:2, 3:2, 2:3, 4:4, 6:6, or $[2:2]_n$. FIGS. 1A-1C illustrate exemplary complexes that could be formed between a multimeric ligand and a monoclonal antibody.

Combination of Multiple mAbs

Figure 2A:
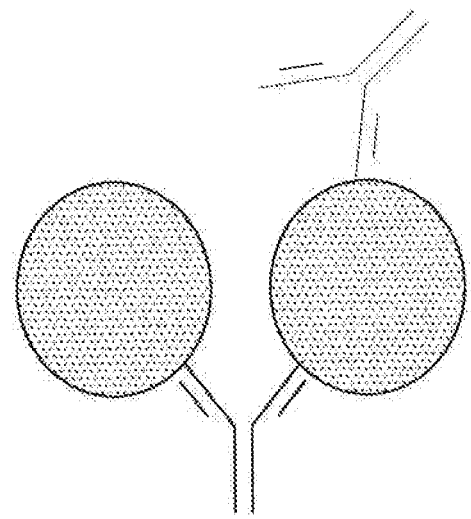
FIGS. 2A-2B are an illustration of a complex formed between antibody 1 (black), two ligands, and antibody 2 (gray) in a non-linear conformation.
Figure 2B:
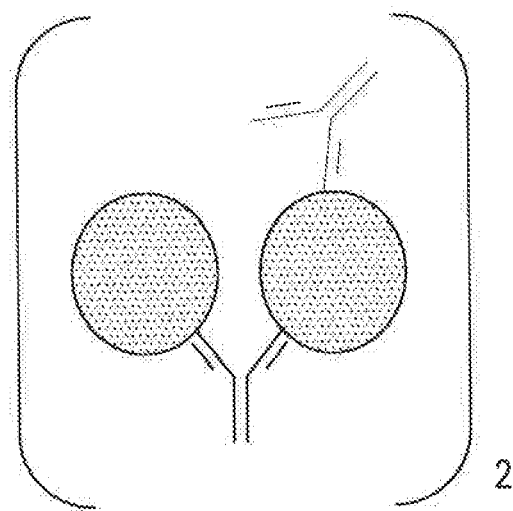
Figure 2C:
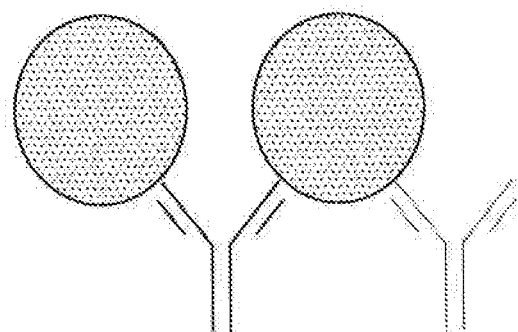
FIGS. 2C-2D are an illustration of an complex formed between antibody 1 (black), two ligands, and antibody 2 (gray) in a linear conformation.
Figure 2D:
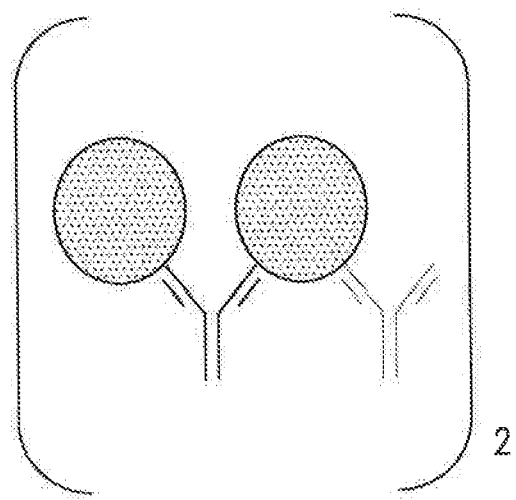

Combination therapy using multiple protein drug products to target the same pathway or the same ligand is growing in popularity. In some embodiments, the disclosed methods can be used to distinguish between different combinations of antibodies targeting the same ligand based on the stoichiometry and size distributions of protein complexes formed by the protein drug products. When two protein drug products are mixed together with a monomeric ligand, the protein drug products have the potential to form a heteromeric complex. A heteromeric complex, as defined herein, refers to two different protein drug products binding the same target molecule. In addition, each of the two arms of the same antibody have the ability to bind two ligands which can also be bound by a second antibody to form a heteromeric complex. FIGS. 2A-2D show representative heteromeric complexes. FIGS. 2A and 2C show complexes formed when one protein drug product (black), or antibody, hinds two ligands and one of the ligands is also bound by a second, unique protein drug product (gray). If the gray protein is hound by another ligand which is then bound by the black protein, larger, more heterogeneous complexes can form, as represented in FIGS. 2B and 2D.

2. Selecting Lead Protein Drug Product

Another embodiment provides a method for selecting a lead protein drug product by adding a first protein drug product to a first sample comprising a target of the first protein drug product to produce heterogeneous protein:ligand complexes and adding a second protein drug product to the a second sample containing the target to form protein:ligand complexes. The method includes separating the heterogeneous protein:ligand complexes and determining the size distribution and stoichiometry of heterogeneous protein:ligand complexes using Asymmetrical flow field flow fractionation—Multi-Angle Laser Light Scattering. The methods also include selecting the protein drug product that forms fewer heterogeneous protein:ligand complexes as the lead target protein drug. In some embodiments, the ligand is a soluble ligand. The soluble ligand can be a monomeric ligand or a multimeric ligand. Typically, the protein drug product is an antibody or antigen binding fragment thereof, a fusion protein, or a recombinant protein. The protein complex can be characterized as a protein complex with an antibody or fusion protein to ligand ratio selected from the group consisting of but not limited to 1:0, 0:1, 1:1, 1:2, 2:1, 2:2, 3:2, 2:3, 4:4, 6:6, or $[2:2]_n$. Another embodiment provides a pharmaceutical composition containing the lead protein drug product selected using the method above.

3. Determining Size and Shape of Protein Complexes

In one embodiment, the disclosed methods can be used to determine the size of protein complexes. A mixture of protein drug products, and optionally soluble ligands, are separated using an A4F fractionation. The size and stoichiometry of the protein complexes can then be determined using MALLS analysis. In MALLS analysis, a beam of polarized light (or a laser) is focused onto the sample molecule and the scattered light is detected with a photo detector. The scattered light is detected at various different angles simultaneously. The intensity of the scattered light at each angle is proportional to the molar mass of the complex. In one embodiment, UV/Vis spectrometry is used to determine the concentration of each protein complex.

In another embodiment, the shape/conformation of a protein complex formed between different protein drug products to a common ligand can be distinguished using the disclosed methods. Differences in elution time or elution profile between complexes with the same molar mass suggest differences in shape or conformation of the protein complexes. Complexes with the same or similar molar mass but with different elution times indicate that the complex with the slower elution time has an increased hydrodynamic volume due to a difference in shape or conformation of the complex.

The size and heterogeneity of the protein complexes can be used to predict the clearance of the protein drug product. In one embodiment, the larger the protein complex, the faster the protein drug product is cleared from the body.

C. Proteins in the Protein Complexes

In one embodiment one of the proteins in the protein complex is a protein drug product or is a protein of interest suitable for expression in prokaryotic or eukaryotic cells. For example, the protein in the protein complexes can be an antibody or antigen-binding fragment thereof, a chimeric antibody or antigen-binding fragment thereof, an ScFv or fragment thereof, an Fe-fusion protein or fragment thereof, a growth factor or a fragment thereof, a cytokine or a fragment thereof, or an extracellular domain of a cell surface receptor or a fragment thereof. Proteins in the complexes may be simple polypeptides consisting of a single subunit, or complex multisubunit proteins comprising two or more subunits. The protein of interest may be a biopharmaceutical product, food additive or preservative, or any protein product subject to purification and quality standards.

In some embodiments, the protein in the protein complexes is an antibody, a human antibody, a humanized antibody, a chimeric antibody, a monoclonal antibody, a multispecific antibody, a bispecific antibody, an antigen binding antibody fragment, a single chain antibody, a diabody, triabody or tetrabody, a dual-specific, tetravalent immunoglobulin G-like molecule, termed dual variable domain immunoglobulin (DVD-IG), an IgD antibody, an IgE antibody, an IgM antibody, an IgG antibody, an IgG1 antibody, an IgG2 antibody, an IgG3 antibody, or an IgG4 antibody. In one embodiment, the antibody is an IgG1 antibody. In one embodiment, the antibody is an IgG2 antibody. In one embodiment, the antibody is an IgG4 antibody. In another embodiment, the antibody comprises a chimeric hinge. In still other embodiments, the antibody comprises a chimeric Fc. In one embodiment, the antibody is a chimeric IgG2/IgG4 antibody. In one embodiment, the antibody is a chimeric IgG2/IgG1 antibody. In one embodiment, the antibody is a chimeric IgG2/IgG1/IgG4 antibody.

In some embodiments, the antibody is selected from the group consisting of an anti-Programmed Cell Death 1 antibody (e.g. an anti-PD1 antibody as described in U.S. Pat. Appln. Pub. No. US2015/0203579A1), an anti-Programmed Cell Death Ligand-1 (e.g., an anti-PD-L1 antibody as described in in U.S. Pat. Appln. Pub. No. US2015/0203580A1), an anti-DI14 antibody, an anti-Angiopoetin-2 antibody (e.g., an anti-ANG2 antibody as described in U.S. Pat. No. 9,402,898), an anti-Angiopoetin-Like 3 antibody (e.g., an anti-AngPtl3 antibody as described in U.S. Pat. No. 9,018,356), an anti-platelet derived growth factor receptor antibody (e.g., an anti-PDGFR antibody as described in U.S. Pat. No. 9,265,827), an anti-Erb3 antibody, an anti-Prolactin Receptor antibody (e.g., anti-PRLR antibody as described in U.S. Pat. No. 9,302,015), an anti-Complement 5 antibody (e.g., an anti-C5 antibody as described in U.S. Pat. Appln. Pub. No US2015/0313194A1), an anti-TNF antibody, an anti-epidermal growth factor receptor antibody (e.g., an anti-EGFR antibody as described in U.S. Pat. No. 9,132,192 or an anti-EGFRvIII antibody as described in U.S. Pat. Appln. Pub. No. US2015/0259423A1), an anti-Proprotein Convertase Subtilisin Kexin-9 antibody (e.g., an anti-PCSK9 antibody as described in U.S. Pat. Nos. 8,062,640 or 9,540,449), an Anti-Growth and Differentiation Factor-8 antibody (e.g. an anti-GDF8 antibody, also known as anti-myostatin antibody, as described in U.S. Pat. Nos. 8,871,209 or 9,260,515), an anti-Glucagon Receptor (e.g. anti-GCGR, antibody as described in U.S. Pat. Appln. Pub. Nos. US2015/0337045A1 or US2016/0075778A1), an anti-VEGF antibody, an anti-IL1R antibody, an interleukin 4 receptor antibody (e.g., an anti-IL4R antibody as described in U.S. Pat. Appln. Pub. No. US2014/0271681A1 or U.S. Pat. Nos. 8,735,095 or 8,945,559), are anti-interleukin 6 receptor antibody (e.g an anti-IL6R antibody as described in U.S. Pat. Nos. 7,582,298, 8,043,617 or 9,173,880), an anti-IL1 antibody, an anti-IL2 antibody, an anti-IL3 antibody, an anti-IL4 antibody, an anti-IL5 antibody, an anti-IL6 antibody, an anti-IL7 antibody, an anti-interleukin 33 (e.g., anti-IL33 antibody as described in U.S. Pat. Nos. 9,453,072 or 9,637,535), an anti-Respiratory syncytial virus antibody (e.g., anti-RSV antibody as described in U.S. Pat. No. 9,447,173), an anti-Cluster of differentiation 3 (e.g., an anti-CD3 antibody, as described in U.S. Pat. Nos. 9,447,173 and 9,447,173, and in U.S. Application No. 62/222,605), an anti-Cluster of differentiation 20 (e.g., an anti-CD20 antibody as described in U.S. Pat. No. 9,657,102 and US20150266966A1, and in U.S. Pat. No. 7,879,984), an anti-CD19 antibody, an anti-CD28 antibody, an anti-Cluster of Differentiation-48 (e.g., anti-CD48 antibody as described in U.S. Pat. No. 9,228,014), an anti-Fel d1 antibody (e.g. as described in U.S. Pat. No. 9,079,948), an anti-Middle East Respiratory Syndrome virus (e.g. an anti-MERS antibody as described in US. Pat. Appln. Pub. No. US201510337029A1), an anti-Ebola virus antibody (e.g. as described in U.S. Pat. Appln. Pub. No. 152016/0215040), an anti-Zika virus antibody, an anti-Lymphocyte Activation Gene 3 antibody (e.g. an anti-LAG3 antibody, or an anti-CD223 antibody), an anti-Nerve Growth Factor antibody (e.g., an anti-NGF antibody as described in U.S. Pat. Appln. Pub. No. US2016/0017029 and U.S. Pat. Nos. 8,309,088 and 9,353,176) and an anti-Protein Y antibody. In some embodiments, the bispecific antibody is selected from the group consisting of an anti-CD3×anti-CD20 bispecific antibody (as described in U.S. Pat. Appln. Pub. Nos. US2014/0088295A1 and US20150266966A1), an anti-CD3×anti-Mucin 16 bispecific antibody (e.g., anti-CD3×anti-Muc16 bispecific antibody), and an anti-CD3×anti-Prostate-specific membrane antigen bispecific antibody (e.g., an anti-CD3× anti-PSMA bispecific antibody). In some embodiments, the protein of interest is selected from the group consisting of abciximab, adalimumab, adalimumab-atto, adotrastuzumab, alemtuzumab, alirocumab, atezolizumab, avelumab, basiliximab, belimumab, benralizumab, bevacizumab, beziotoxumab, blinatunromab, brentuximab vedotin, brodalumab canakinumab, capromab pendetide, certolizumab pegol, cemiplimab, eetuximab, denosumab, dinutuximab, dupilumab, durvalumab, eculizumab, elotuzumab, emieizumab-kxwh, emtansinealirocumab, evinacumab, evolocumab, fasinumab, golimumab, guselkumab, ibriturnomab tiuxetan, idarucizumab, infliximab, infliximab-abda, infliximab-dyyb, ipilimumab, ixekizumab, mepolizumab, necitumumab, nesvacumab, nivolumab, obiltoxaximab, obinutuzumab, ocrelizumab, ofatumumab, olaratumab, omalizumab, panitumumab, pembrolizumab, pertuzumab, ramucirumab, ranibizumab, raxihacumab, reslizumab, rinueumab, rituximab, sarilumab, secukinumab, siltuximab, tocilizumab, tocilizurnab, trastuzumab, trevogrumab, ustekinumab, and vedolizumab.

In some embodiments, the protein in the complexes is a recombinant protein that contains an Fc moiety and another domain, (e.g., an Fe-fusion protein). In some embodiments, an Fc-fusion protein is a receptor Fc-fusion protein, which contains one or more extracellular domain(s) of a receptor coupled to an Fc moiety. In some embodiments, the Fc moiety comprises a hinge region followed by a CH2 and CH3 domain of an IgG. In some embodiments, the receptor Fc-fusion protein contains two or more distinct receptor chains that bind to either a single ligand or multiple ligands. For example, an Fc-fusion protein is a TRAP protein, such as for example an IL-1 trap (e.g., rilonacept, which contains the IL-1RAcP ligand binding region fused to the Il-1R1 extracellular region fused to Fc of hIgG1; see U.S. Pat. No. 6,927,004, which is herein incorporated by reference in its entirety), or a VEGF trap (e.g., aflibercept or ziv-aflibercept, which comprises the Ig domain 2 of the VEGF receptor Flt1 fused to the Ig domain 3 of the VEGF receptor Flk1 fused to Fc of hIgG1; see U.S. Pat. Nos. 7,087,411 and 7,279,159).

In other embodiments, an Fe-fusion protein is a ScFv-Fc-fusion protein, which contains one or more of one or more antigen-binding domain(s), such as a variable heavy chain fragment and a variable light chain fragment, of an antibody coupled to an Fc moiety.

EXAMPLES

Example 1: A4F Analysis Offers Superior Resolution for Samples Containing Large, Heterogeneous Complexes Compared to SEC Fractionation Methods SEC-MALLS Mobile Phase Buffer The mobile phase buffer (10 mM sodium phosphate, 500 mM sodium chloride, pH 7.0±0.1) was prepared by combining 4.23 g sodium phosphate monobasic monohydrate, 5.20 g sodium phosphate dibasic heptahydrate, and 500 mL 5 M sodium chloride; the solution was then brought to a volume to 5.0 L with HPLC grade water. The final measured pH of the buffer was 7.0. The mobile phase buffer was filtered (0.2 µm) before use.

SEC-MALLS Analysis

The SEC-MALLS system is composed of a Superose 6 GL column (10 mm×300 mm; GE Healthcare, cat # 17-5172-01), coupled to an Agilent 1200 Series HPLC system equipped with a ultraviolet (UV) diode array detector, Wyatt Technology miniDawn TREOS® laser light scattering instrument (LS), and an Optilab® T-rEX differential refractometer (RI) detector. The detectors were connected in series in the following order: UV-LS-RI. LS and RI detectors were calibrated according to instructions provided by Wyatt Technology.

Defined amounts of anti-ProteinX mAb were each combined with recombinant ProteinX and diluted in 1×DPBS, pH 7.4 to yield the following molar ratios: 5 µM anti-ProteinX mAb: 1 µM ProteinX, 1 µM anti-:ProteinX mAb: 1 µM ProteinX, and 1 µM anti-ProteinX mAb: 5 µM ProteinX. All samples were incubated at ambient temperature for 2 hours and maintained unfiltered at 4° C. prior to injection into the column. The column was pre-equilibrated with the mobile phase buffer (10 mM sodium phosphate, 500 mM sodium chloride, pH 7.0±0.1) at a flow rate of 0.3 mL/min, prior to the injection of each sample. Bovine serum albumin (BSA; 2 mg/mL; 150 µg sample load) was injected separately and included as a system suitability control.

The SEC-MALLS mobile phase buffer (10 mM sodium phosphate, 500 mM sodium chloride, pH 7.0±0.1) was used throughout the fractionation. Each sample (100~200 µg) was injected, and was eluted with a flow rate of 0.3 mL/min. BSA was fractionated using the same parameter settings.

A4F-MALLS Mobile Phase Buffer

The mobile phase buffer (10 mM sodium phosphate, 500 mM sodium chloride, pH 7.0±0.1) was prepared by combining 4.23 g sodium phosphate monobasic monohydrate, 5.20 g sodium phosphate dibasic heptahydrate, and 500 ml 5 M sodium chloride; the solution was then brought to a volume to 5.0 L with HPLC grade water. The final measured pH of the buffer was 7.0. The mobile phase buffer was filtered (0.2 µm) before use.

A4F-MALLS

The A4F-MALLS system was composed of an Eclipse™ 3+ A4F Separation System coupled to an Agilent 1200 Series HPLC system equipped with a ultraviolet (UV) diode array detector, Wyatt Technology Dawn HELEOS® II laser light scattering instrument (LS), and an Optilab® T-rEX differential refractometer (RI) detector. The detectors were connected in series in the following order: UV-LS-RI. LS and RI detectors were calibrated according to instructions provided by Wyatt Technology.

Defined amounts of anti-ProteinX mAb were each combined with recombinant ProteinX and diluted in 1×DPBS, pH 7.4 to yield the following molar ratios: 5 µM anti-ProteinX mAb: 1 µM ProteinX, 2 µM anti-ProteinX mAb: 1 µM ProteinX, and 1 µM anti-ProteinX mAb: 1 µM ProteinX. All samples were incubated at ambient temperature for 2 hours and maintained unfiltered at 4° C. prior to injection into an Eclipse™ short channel fitted with a W350 spacer foil (350 µm spacer thickness, 2.2 cm spacer width) and using a 10 kDa MWCO Nadir regenerated cellulose membrane. The channel was pre-equilibrated with the mobile phase buffer (10 mM sodium phosphate, 500 mM sodium chloride, pH 7.0±0.1), prior to the injection of each sample. Bovine serum albumin (BSA; 2 mg/mL; 10 µg sample load) was injected separately and included as a system suitability control.

The fractionation method consisted of four steps: injection, focusing, elution, and a channel "wash-out" step. The A4F-MALLS mobile phase buffer (10 mM sodium phosphate, 500 mM sodium chloride, pH 7.0±0.1) was used throughout the fractionation method. Each sample (7 µg) was injected at a flow rate of 0.2 mL/min for 1 min and subsequently focused for 2 min with a focus flow rate of 1.5 mL/min. The sample was eluted with a channel flow rate of 1.0 mL/min with the linear gradient cross flow from 3.0 mL/min to 0 mL/min over 45 min. Finally, the cross flow was held at 0 mL/min for an additional 5 min to wash out the channel. BSA was fractionated using the same parameter settings.

MALLS Data Analysis

Data were analyzed using ASTRA V software (version 5.3.4.14, Wyatt Technology). The data were fit to the equation that relates the excess scattered light to the solute concentration and weight-average molar mass, Mw, (Wyatt, 1993; Kendrick, 2001)

$$\frac{K^*c}{R(\theta, c)} = \frac{1}{MwP(\theta)} + 2A_2c \qquad \text{Equation 1}$$

where c is the solute concentration, R(θ,c) is the excess Raleigh ratio from the solute as a function of scattering angle and concentration, Mw is the molar mass, P(θ) describes the angular dependence of scattered light (~1 for particles with radius of gyration <50 nm), $A_2$ is the second virial coefficient in the expansion of osmotic pressure (which can be neglected since measurements are performed on dilute solutions) and $$K^* = \frac{4\pi^2 n_0^2}{N_A \lambda_0^4} \left(\frac{dn}{dc}\right)^2 \qquad \text{Equation 2}$$

where $n_o$ represents the solvent refractive index, $N_A$ is Avogadro's number, $\lambda_0$ is the wavelength of the incident light in a vacuum, and dn/dc represents the specific refractive index increment for the solute.

The molar mass of BSA monomer served to evaluate the calibration constants of the light scattering and differential refractive index detectors during data collection (system suitability check). The relative standard deviation (% RSD) of the average molar mass of BSA determined from the UV and RI detectors was ≤5.0%.

The normalization coefficients for the light scattering detectors, inter-detector delay volume and band broadening terms were calculated from the BSA chromatograms collected for the A4F-MALLS condition employed. These values were applied to the data files collected for all the other samples to correct for these terms.

The dn/dc value and the extinction coefficient at 215 nm or 280 nm (corrected for glycosylation) were experimentally determined using the protein conjugate analysis provided in the Astra software. The corrected extinction coefficient and dn/dc value was used to analyze all protein-protein complex samples.

Results

Figure 3A:
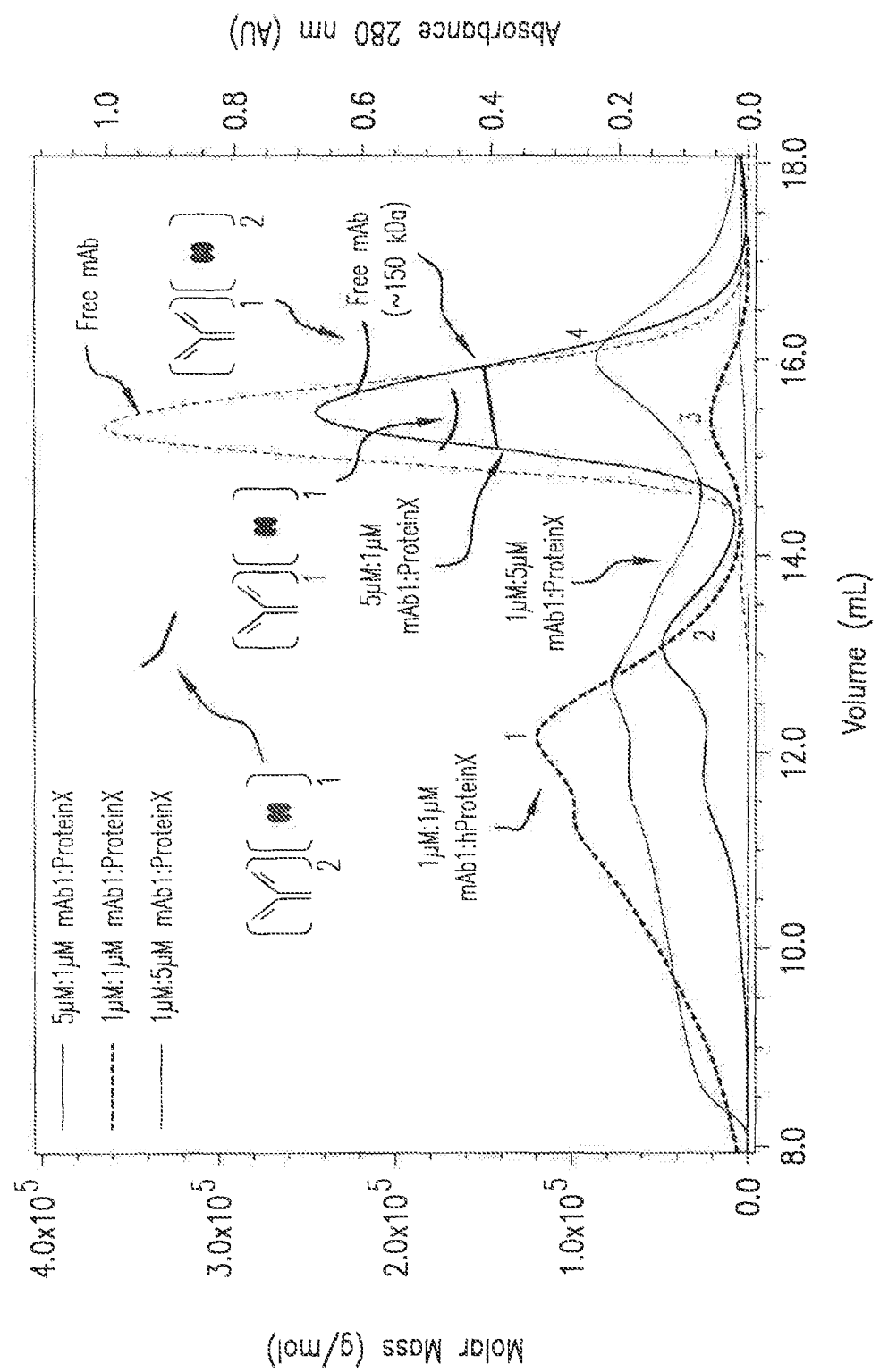
FIG. 3A is a chromatogram from SEC-MALLS analysis of Ab1, Protein X, and combinations of Ab1 and Protein X at ratios of 5:1, 1:1, and 1:5. The X axis represents elution time (minutes). The left Y axis represents molar mass (g/mol) and the right Y axis represents absorbance at 280 nm (AU).
Figure 3B:
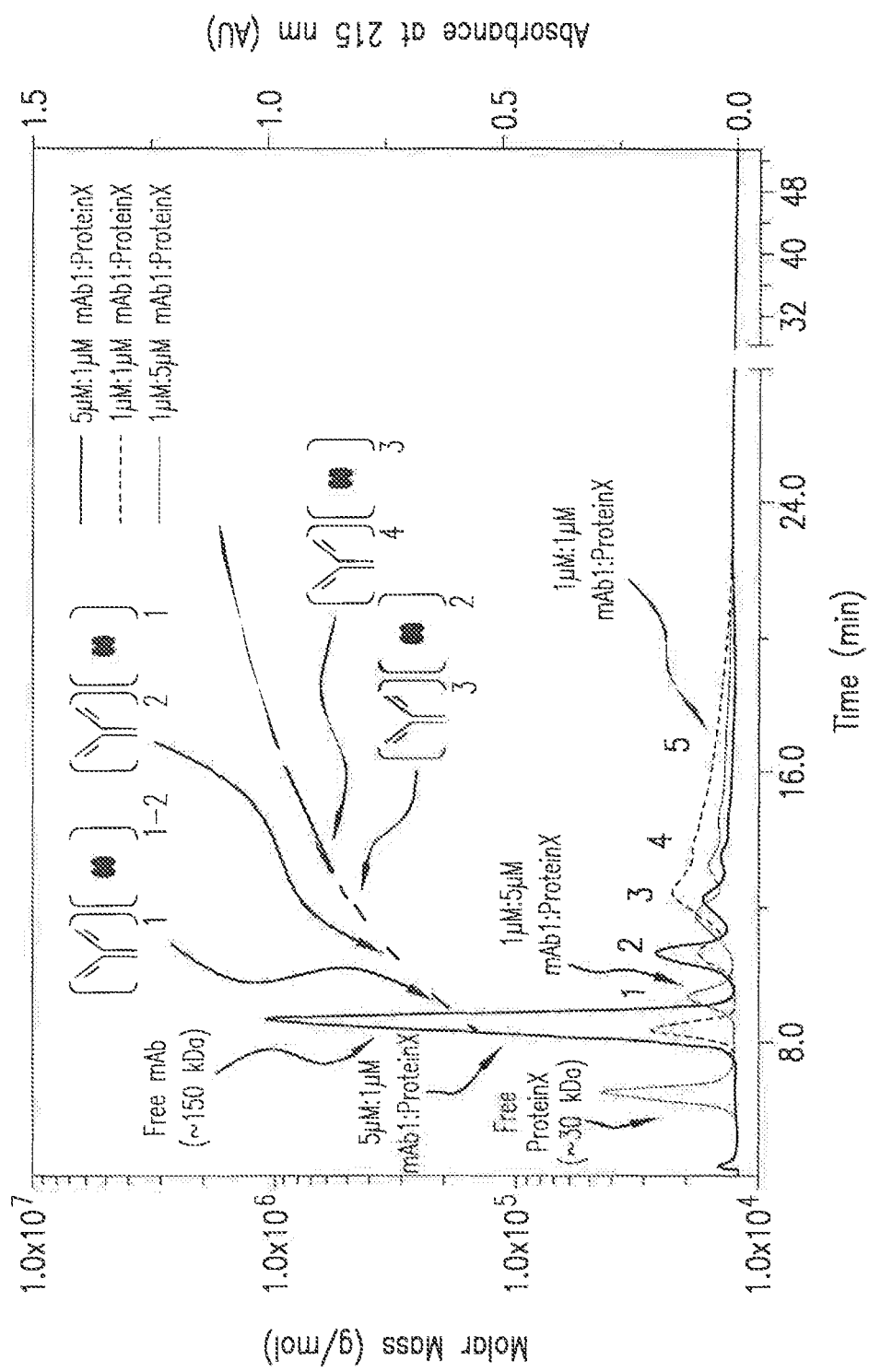
FIG. 3B is a fractogram from A4F-MALLS analysis of combinations of Ab1 and Ab2 at ratios of 5:1, 2:1, and 1:1. The X axis represents elution time (minutes). The left Y axis represents molar mass (g/mol). The right Y axis represents absorbance at 215 nm (AU).

SEC-MALLS analysis of the samples showed poor resolution of higher order complexes (elution volume=8-14 mL) and no distinction of intermediate complexes (FIG. 3A, Table 1). In contrast, A4F-MALLS analysis of the samples showed superior resolution of higher order complexes (elution volume=~11-30 mL) and clear distinction of intermediate complexes (FIG. 3B, Table 2).

TABLE 1

Approximate molar mass and retention time for mAb:Protein X complexes.

| Sample | Molar Ratio (mol:mol) | Peak 1 Higher Order Complexes | | Peak 2 [Intact Antibody]$_2$: [ProteinX]$_1$ Complex | | Peak 3 [Intact Antibody]$_1$: [ProteinX]$_1$ Complex | | Peak 4 [Intact Antibody]$_1$: [ProteinX]$_2$ Complex | |
|---|---|---|---|---|---|---|---|---|---|
| | | $R_t$, min | $M_w$, kDa | $R_t$, min | $M_w$, kDa | $R_t$, min | $M_w$, kDa | $R_t$, min | $M_w$, kDa |
| mAb1:ProteinX | 5:1 | 9.0-12.6 | ~390-1000 | 13.1 | 330.7 | NA | NA | NA | NA |
| mAb1:ProteinX | 1:1 | 8.0-13.4 | ~400-3000 | NA | NA | 15.4 | 166.9 | NA | NA |
| mAb1:ProteinX | 1:5 | 8.5-13.8 | ~430-2000 | NA | NA | NA | NA | 16.0 | 216.3 |

$R_t$: Retention Time;
$M_w$: weight average molar mass;
NA: Not Applicable;
min: minutes;
kDa: kiloDaltons;

TABLE 2

Approximate molar mass and retention time for mAb:Protein X complexes

| | | Peak 1 [Intact Antibody]$_1$: [ProteinX]$_{1-2}$ Complex | | Peak 2 [Intact Antibody]$_2$: [ProteinX]$_1$ Complex | | Peak 3 [Intact Antibody]$_3$: [ProteinX]$_2$ Complex | | Peak 4 [Intact Antibody]$_4$: [ProteinX]$_3$ Complex | | Peak 5 Higher Order Complexes | |
|---|---|---|---|---|---|---|---|---|---|---|---|
| Sample | Molar Ratio (mol:mol) | $R_t$, min | $M_w$, kDa | $R_t$, min | $M_w$, kDa | $R_t$, min | $M_w$, kDa | $R_t$, min | $M_w$, kDa | $R_t$, min | $M_w$, kDa |
| mAb1:ProteinX | 5:1 | NA | NA | 10.8 | 321.1 | 12.4 | 497.8 | 13.7 | 673.8 | 14.6 | 830–1190 |
| mAb1:ProteinX | 1:1 | NA | NA | 10.7 | 332.8 | 12.5 | 514.8 | 13.7 | 671.3 | 14.6 | 780–1620 |
| mAb1:ProteinX | 1:5 | 9.4 | 191.1 | NA | NA | 11.8 | 461.1 | 13.3 | 599.7 | 14.4 | 720–1180 |

$R_t$: Retention Time;

$M_w$: weight average molar mass;

NA: Not Applicable;

min: minutes;

kDa: kiloDaltons;

Example 2: Anti-Protein Y Complexes

Methods

A4F MALLS Mobile Phase Buffer

1×DPBS, pH 7.4, was prepared by diluting 500 mL of 10×DPBS with HPLC grade water to a total volume of 4.9 L. A solution of 0.0025% (w/v) sodium azide was added as an antimicrobial agent. Hydrochloric acid (12 M) was slowly added in small volume increments to adjust the pH to 7.4 before bringing the final volume to 5.0 L. The final, measured pH of the buffer was 7.4. The buffer solution was prepared fresh and filtered (0.2 μm) prior to use.

A4F MALLS Analysis

Defined amounts of anti-Protein mAbs (Lead A and Lead B) were each combined with recombinant human Protein Y and diluted in 1×DPBS, pH 7.4 to yield the following molar ratios: 1 μM anti-Protein Y mAb: 3 μM hActA, 1 μM anti-Protein Y mAb: 1 μM Protein Y, and 3 μM anti-Protein Y mAb: 1 μM Protein Y. All samples were incubated at ambient temperature for 2 hours and maintained unfiltered at 4° C. prior to injection into an Eclipse™ short channel fitted with a W490 spacer foil (490 μm spacer thickness, 2.2 cm spacer width) and using a 10 kDa MWCO Nadir regenerated cellulose membrane. The channel was pre-equilibrated with 1× DPBS buffer, pH 7.4, prior to the injection of each sample. Bovine serum albumin (BSA; 2 mg/mL; 10 μg sample load) was injected separately and included as a system suitability control.

The fractionation method consisted of four steps: injection, focusing, elution, and a channel "wash-out" step. The A4F-MALLS mobile phase buffer (1×DPBS, pH 7.4) was used throughout the fractionation method. Each sample (10 μg) was injected at a flow rate of 0.2 mL/min for 1 min and subsequently focused for 2 min with a focus flow rate of 1.5 mL/min. The sample was eluted with a channel flow rate of 1.0 mL/min with the linear gradient cross flow from 1.2 mL/min to 0 mL/min over 20 min. Finally, the cross flow was held at 0 mL/min for an additional 5 min to wash out the channel. BSA was fractionated using the same parameter settings.

Mouse Anti-Human Antibody Titer

Mouse anti-human antibody (MAHA) titers were determined using a sandwich ELISA specific for the detection of mAb A or mAb B mouse IgG. Briefly, mAb A or mAb B at 1 μg/mL in phosphate-buffered saline (PBS) were passively adsorbed to a microtiter plate overnight at 4° C., followed by a nonspecific binding block with 5% bovine serum albumin (BSA) in PBS. Serial dilutions of serum samples were prepared in dilution buffer (0.5% BSA in PBS) starting from 1:100. Therefore, the corresponding dilution factor (100) was defined as the assay's lower limit of detection (LOD). Samples were then added to the mAb A or mAb B coated plate (100 μL/well) and incubated 16-18 hours at 4° C. Wells with addition of dilution buffer only were included to determine background signal. Subsequently, plate-captured mAb A or mAb B-specific MAHA was detected using horseradish peroxidase (HRP)-conjugated anti-mouse Fcγ at 40 ng/mL. The chromogenic HRP-substrate, 3,3',5,5'-tetramethylbenzidine (TMB) was used to detect HRP activity; and the resultant optical density at 450 nm (OD$_{45}$) was read on a Perkin Elmer Victor X4 Multimode Plate Reader. Data of binding signal versus dilution factor were analyzed by non-linear regression using GraphPad Prism software and titers were calculated. The MAHA titer was defined as the calculated dilution factor of the serum sample corresponding to a binding signal equivalent to twice the background signal of the assay.

Results

Figure 4A:
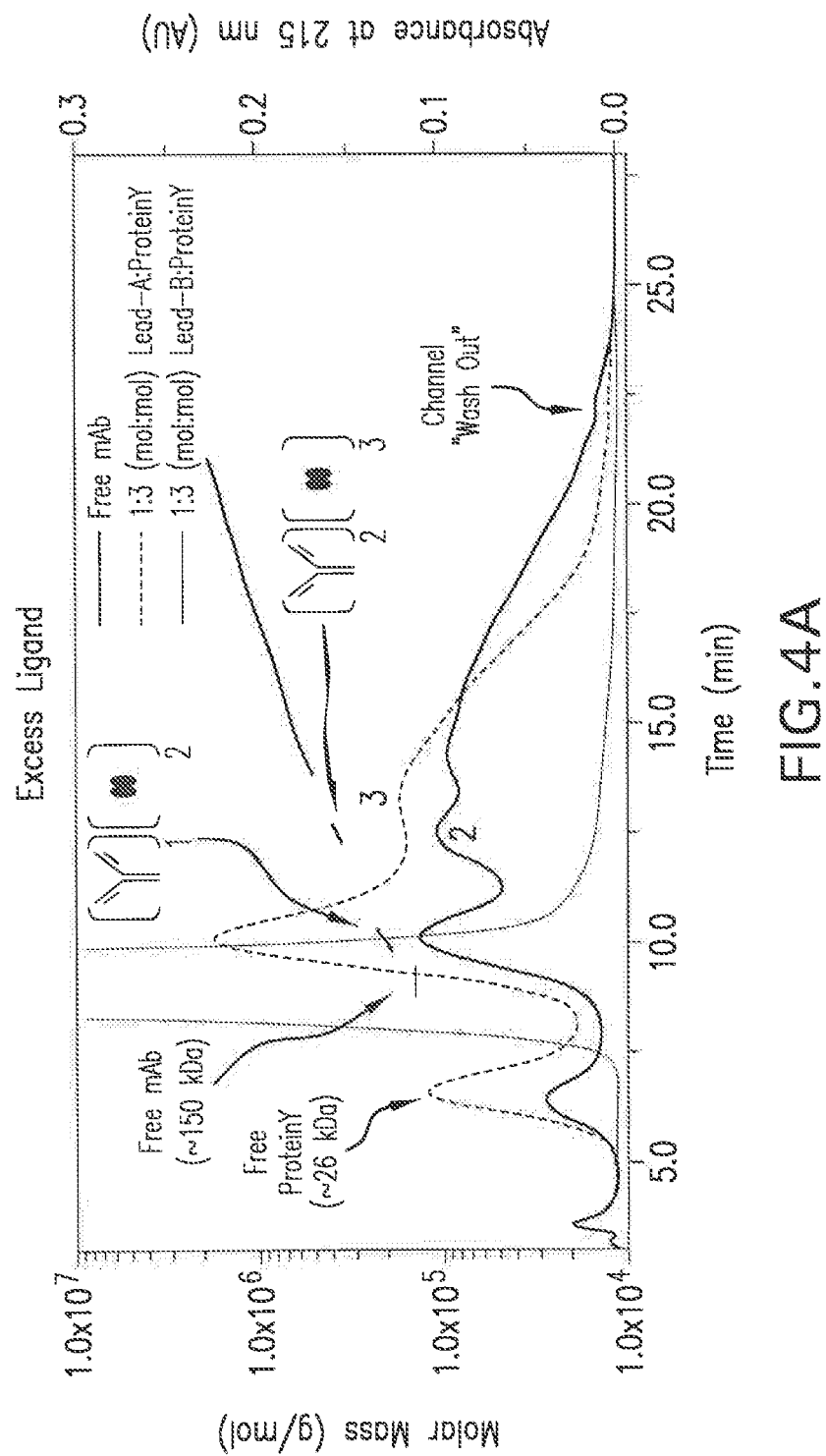
FIG. 4A is a fractogram from A4F-MALLS analysis of lead compound A (Lead A), Lead A+Protein Y (1:3), and Lead compound B (Lead B)+Protein Y (1:3).
Figure 4B:
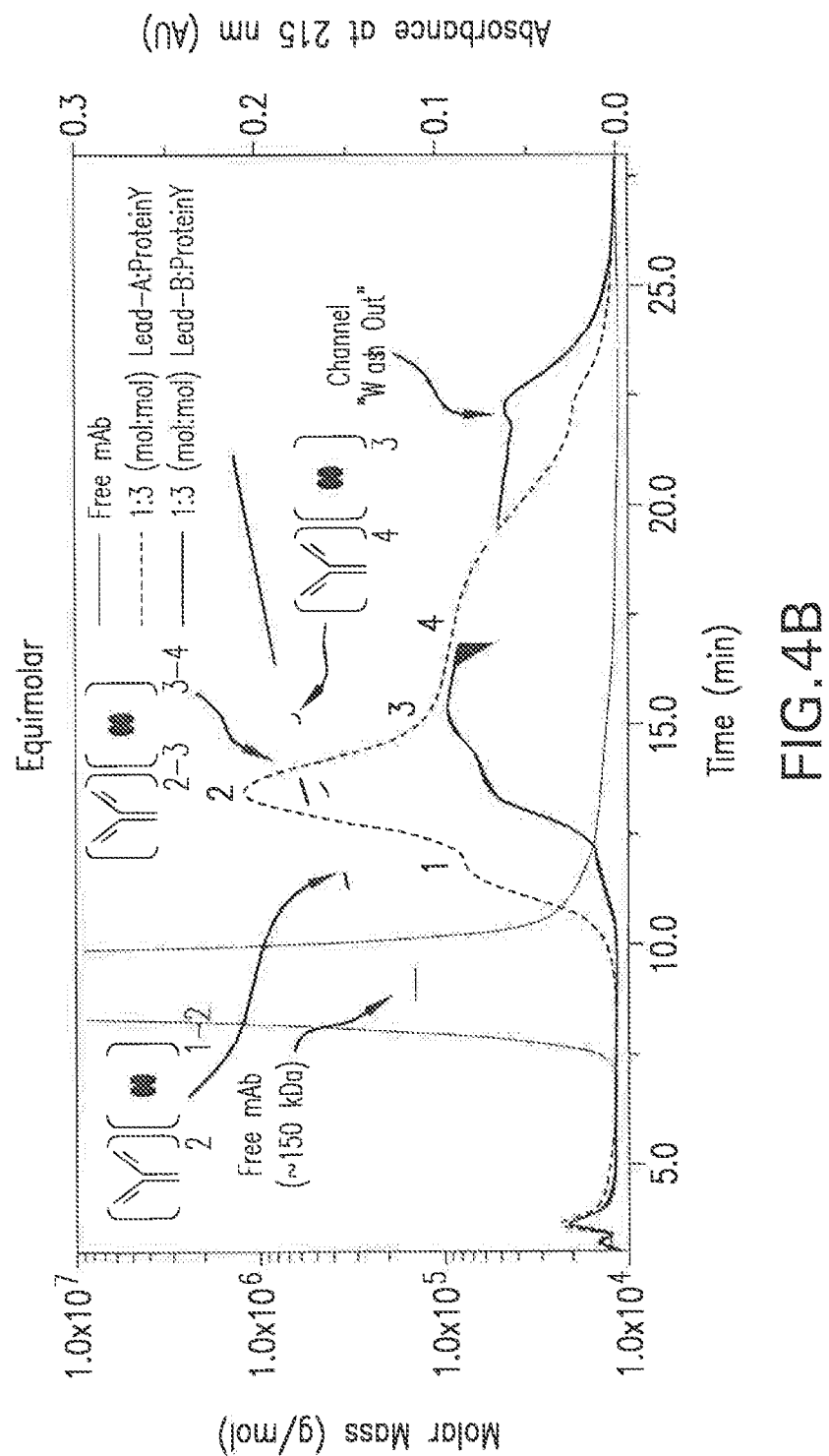
FIG. 4B is a fractogram from A4F-MALLS analysis of Lead A, Lead A+Protein Y (1:1), and Lead B+Protein Y (1:1).
Figure 4C:
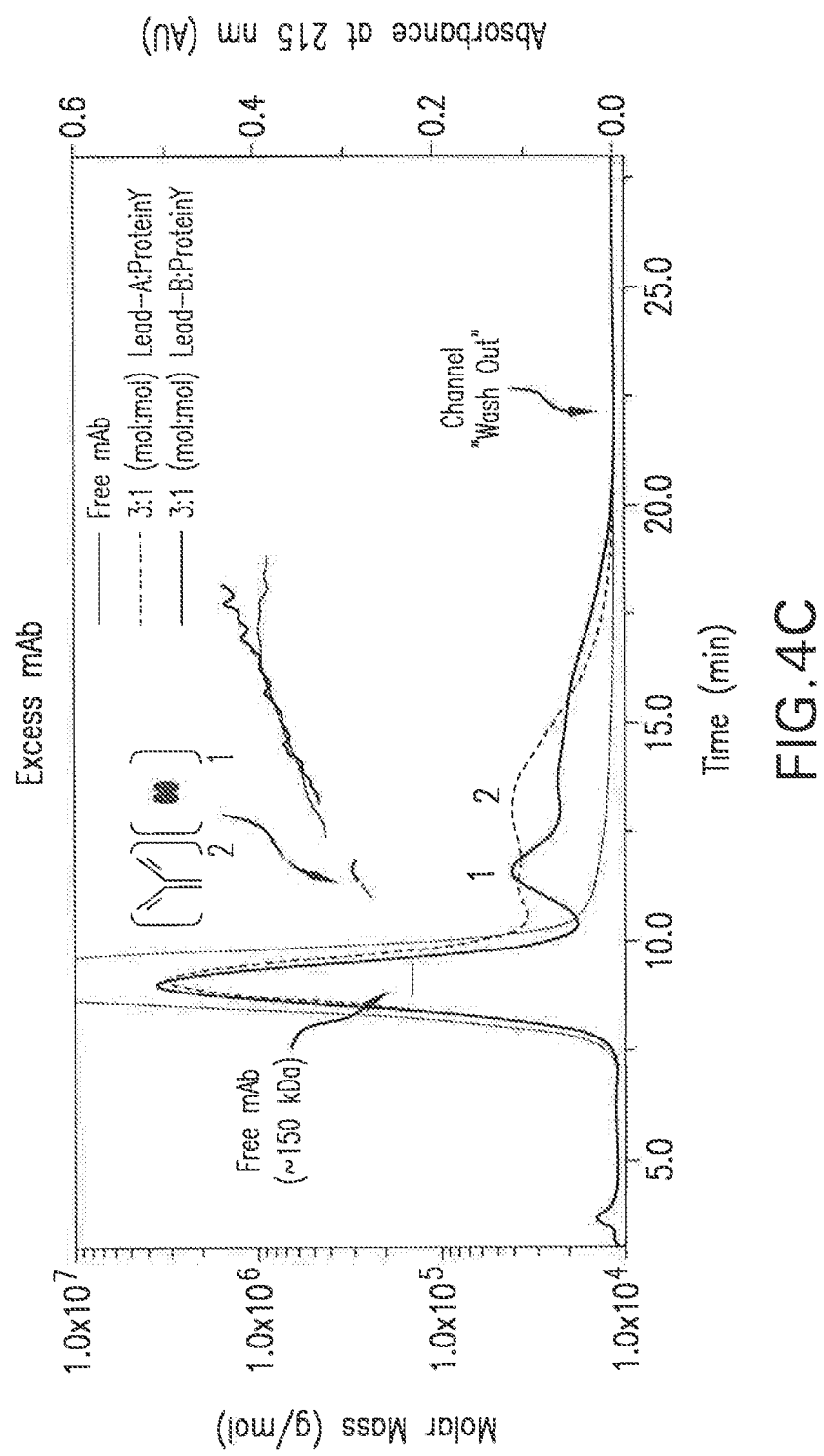
FIG. 4C is a fractogram from A4F-MALLS analysis of Lead A, Lead A+Protein Y (3:1), and Lead B+Protein Y (3:1). The X axis represents time (minutes). The left Y axis represents molar mass (g/mol) and the right Y axis represents absorbance at 280 nm (AU).

The two lead mAbs formed distinctly different complexes with Protein Y. Under all conditions tested, mAb Lead-A formed smaller, less heterogeneous complexes with Protein Y than mAb Lead-B (FIGS. 4A-4C, Tables 3-5).

TABLE 3

Approximate molar mass and retention time for mAb:Protein Y complexes.

| Sample | Molar Ratio (mol:mol) | Peak 1 [Intact Antibody]$_1$:[ProteinY]$_2$ Complex | | Peak 2 [Intact Antibody]$_2$:[ProteinY]$_3$ Complex | | Peak 3 Higher Order Complexes | |
|---|---|---|---|---|---|---|---|
| | | $R_t$, min | $M_w$, kDa | $R_t$, min | $M_w$, kDa | $R_t$, min | $M_w$, kDa |
| Lead-A:ProteinY | 1:3 | 10.1 | 215.9 | NA | NA | 13.1 | ~500-1000 |
| Lead-B:ProteinY | 1:3 | 10.1 | 219.1 | 12.5 | 390.1 | 14.3 | ~550-2000 |

$R_t$: Retention Time;
$M_w$: weight average molar mass;
NA: Not Applicable;
min: minutes;
kDa: kiloDaltons;

TABLE 4

Approximate molar mass and retention time for mAb:Protein Y complexes.

| Sample | Molar Ratio (mol:mol) | Peak 1 [Intact Antibody]$_2$:[ProteinY]$_{1-2}$ Complex | | Peak 2 [Intact Antibody]$_{2-3}$:[ProteinY]$_{3-4}$ Complex | | Peak 3 [Intact Antibody]$_4$:[ProteinY]$_3$ Complex | | Peak 4 Higher Order Complexes | |
|---|---|---|---|---|---|---|---|---|---|
| | | $R_t$, min | $M_w$, kDa | $R_t$, min | $M_w$, kDa | $R_t$, min | $M_w$, kDa | $R_t$, min | $M_w$, kDa |
| Lead-A:ProteinY | 1:1 | 11.9 | 347.7 | 13.5 | 589.4 | NA | NA | 16.5 | ~850-1400 |
| Lead-B:ProteinY | 1:1 | NA | NA | 14.0 | 448.7 | 15.3 | 635.9 | 16.4 | ~815-2300 |

$R_t$: Retention Time;
$M_w$: weight average molar mass;
NA: Not Applicable;
min: minutes;
kDa: kiloDaltons;

TABLE 5

Approximate molar mass and retention time for mAb:Protein Y complexes.

| Sample | Molar Ratio (mol:mol) | Peak 1 [Intact Antibody]$_2$:[ProteinY]$_1$ Complex | | Peak 2 Higher Order Complexes | |
|---|---|---|---|---|---|
| | | $R_t$, min | $M_w$, kDa | $R_t$, min | $M_w$, kDa |
| Lead-A:ProteinY | 3:1 | 11.3 | 265.3 | 13.0 | ~400-900 |
| Lead-B:ProteinY | 3:1 | 11.6 | 306.9 | 12.9 | ~480-1600 |

Figure 5A:
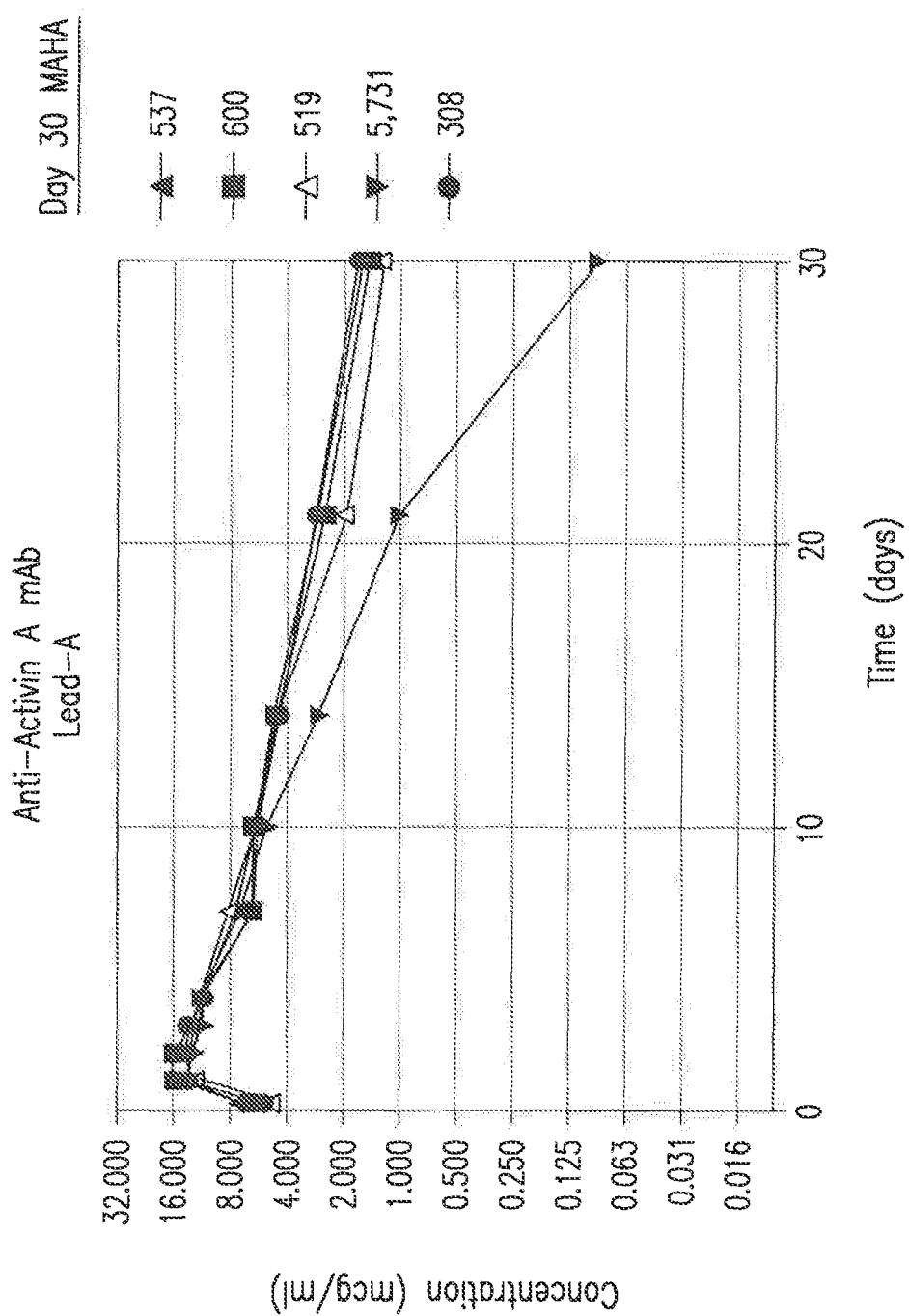
FIGS. 5A and 5B are line graphs of mouse anti-human antibody titer of anti-Protein Y complexes with Lead A (FIG. 5A) and Lead B (FIG. 5B). The X axis represents time (days) and the Y axis represents concentration (µg/ml).
Figure 5B:
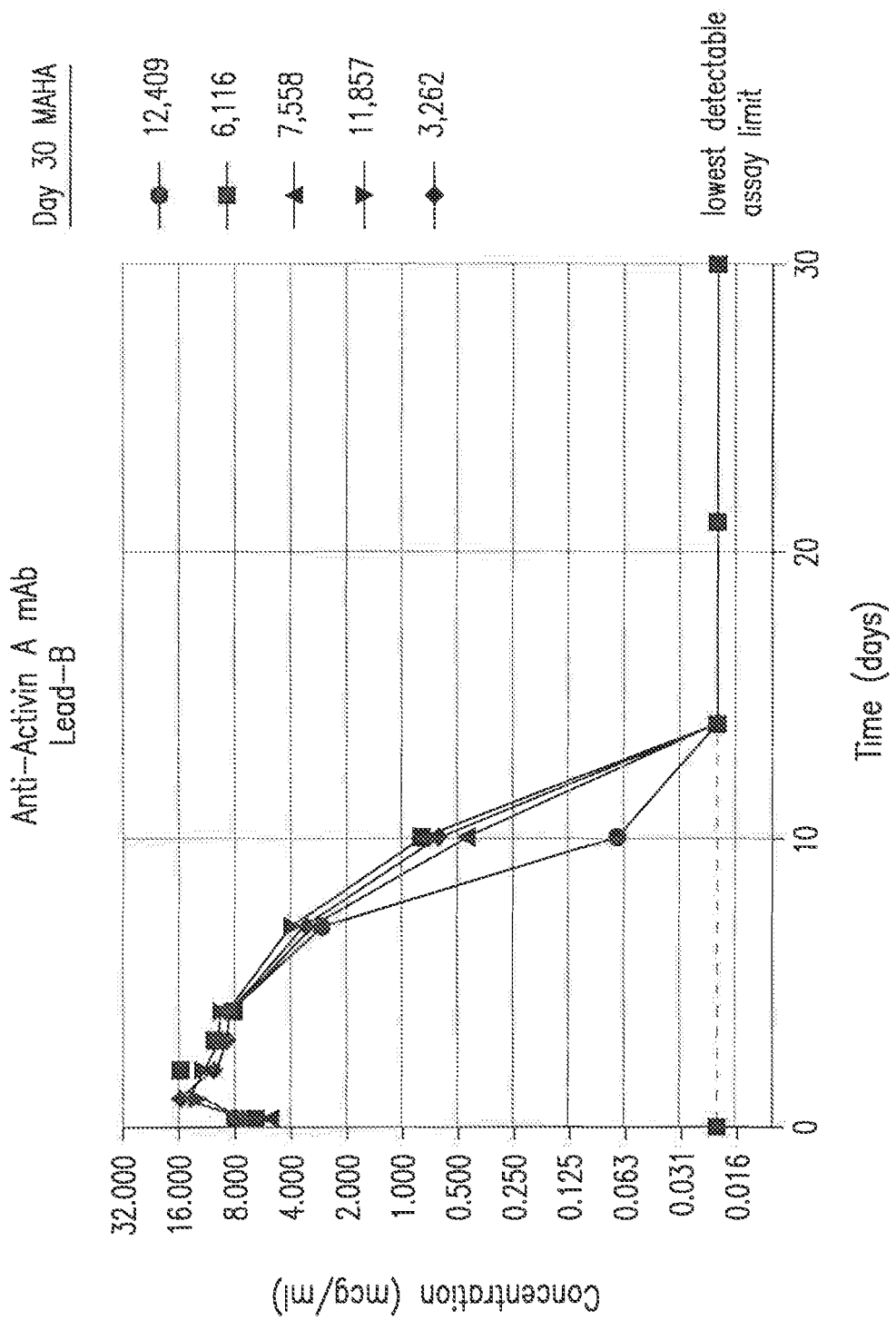

$R_t$: Retention Time;
$M_w$: weight average molar mass;
NA: Not Applicable;
min: minutes;
kDa: kiloDaltons;

The size and heterogeneity of anti-Protein Y complexes correlated well with mouse PK observations (FIGS. 5A-5B). Larger complexes observed for Lead-B with Protein Y correlated with faster clearance (FIG. 5B).

Example 3: Anti-Human Protein Z Complexes

Methods
Sample Preparation
Samples were prepared in 1×DPBS, pH 7.4 and allowed to incubate at room temperature for 2 hrs. prior to fractionation of total protein by A4F-MALLS. The samples were as follows: 1 mM anti-Protein Z mAb1+Secondary mAb (0.5 mM+0.5 mM)+1 mM complement Protein Z (7 combinations) or 1 mM anti-Protein Z mAb6+ anti-Protein Z mab7 (0.5 mM+0.5 mM)+1 mM complement Protein Z. The list of secondary antibodies can be found in Table 6.

TABLE 6

Sample Nomenclature.

| Secondary mAbs Tested | Nomenclature Combo with anit-Protein Z mAb1 |
|---|---|
| anti-Protein Z mAb2 | mAb2 Combo |
| anti-Protein Z mAb3 | mAb3 Combo |
| anti-Protein Z mAb4 | mAb4 Combo |
| anti-Protein Z mAb5 | mAb5 Combo |
| anti-Protein Z mAb5 | mAb6 Combo |
| anti-Protein Z mAb7 | mAb7 Combo |
| COMP1 mAb | COMP1 Combo |

A4F MALLS Analysis

All samples were incubated at ambient temperature for total of 2 hours and maintained unfiltered at 4° C. prior to injection into an Eclipse™ short channel fitted with a W350 spacer foil (350 µm spacer thickness, 2.2 cm spacer width) and using a 4 kDa MWCO hydrophilic PES (PESH) membrane. The channel was pre-equilibrated with the mobile phase buffer (10 mM sodium phosphate, 500 sodium chloride, pH 7.0±0.1), prior to the injection of each sample. BSA (2 mg/mL; 10 µg sample load) was injected separately and included as a system suitability control.

The fractionation method consisted of four steps: injection, focusing, elution, and a channel "wash-out" step. The A4F-MALLS mobile phase buffer (10 mM sodium phosphate, 500 mM sodium chloride, pH 7.0±0.1) was used throughout the fractionation method. Each sample (7 µg complex or 4 µg individual component) was injected at a flow rate of 0.2 mL/min and focused for 5 min with a focus flow rate of 1 mL/min. The sample was eluted with a channel flow rate of 1 mL/min with the linear gradient cross flow from 2 mL/min to 0 mL/min over 45 min. Finally, the cross flow was held at 0 mL/min for an additional 5 min to wash out the channel. BSA was fractionated using the same parameter settings.

RBC Hemolysis Assay

Alternative pathway hemolysis assay was used as the measure of complement activation to evaluate the ability of anti-Protein Z mAbs to block the lysis of rabbit red blood cells (RbRBCs). Lysis of rabbit red blood cells by membrane attack complex is the basis of the assay by which complement activation is experimentally measured.

A desired number of RbRBCs are washed in GVB-M2+/EGTA buffer and re suspended at $2 \times 10^8$ cell/ml. To test the efficacy of either single anti-C5 mAb or combination of anti-C5 mAbs, normal human serum was diluted to 50-96% in GVB-$Mg^{2+}$/EGTA buffer to achieve a final concentration of 25-48% when added to RBC. Round bottom 96 well plates were used to measure hemolysis activity. A total of 100 ul RbRBCs ($2 \times 10^8$ cells/ml) were plated into 96-well plate at 37° C. followed by addition of 100 ul of diluted serum. Cells were gently mixed and incubated at 37° C. for 30-120 minutes. After incubation time, the cells were spun down by centrifugation at 1250×g at 4° C. A total of 100 uL of the supernatant was transferred to a fresh 96 flat bottom plate and read at 412 nm on a Spectramax microplate reader. The calculation of percent of hemolysis was done as described below.

The percentage of hemolysis was calculated with the absorbance values by using the following equation:

$$\% \text{ Hemolysis} = 100 \times \frac{(\text{Experimental Cell Lysis} - \text{Background Cell Lysis})}{(\text{Maximum Cell Lysis} - \text{Background Cell Lysis})} \quad \text{Equation 3}$$

In this equation "background cell lysis" is the OD at A412 nm from the cells incubated in GVB-$Mg^{2+}$/EGTA buffer only containing no serum. The "maximum cell lysis" is the OD at A412 nm from the cells treated with water. Maximum inhibition of lysis was calculated as a difference between bottom and top values in the curve expressed as a percentage of top value. Data represented as mean±Standard error of mean.

Results

Figure 6A:
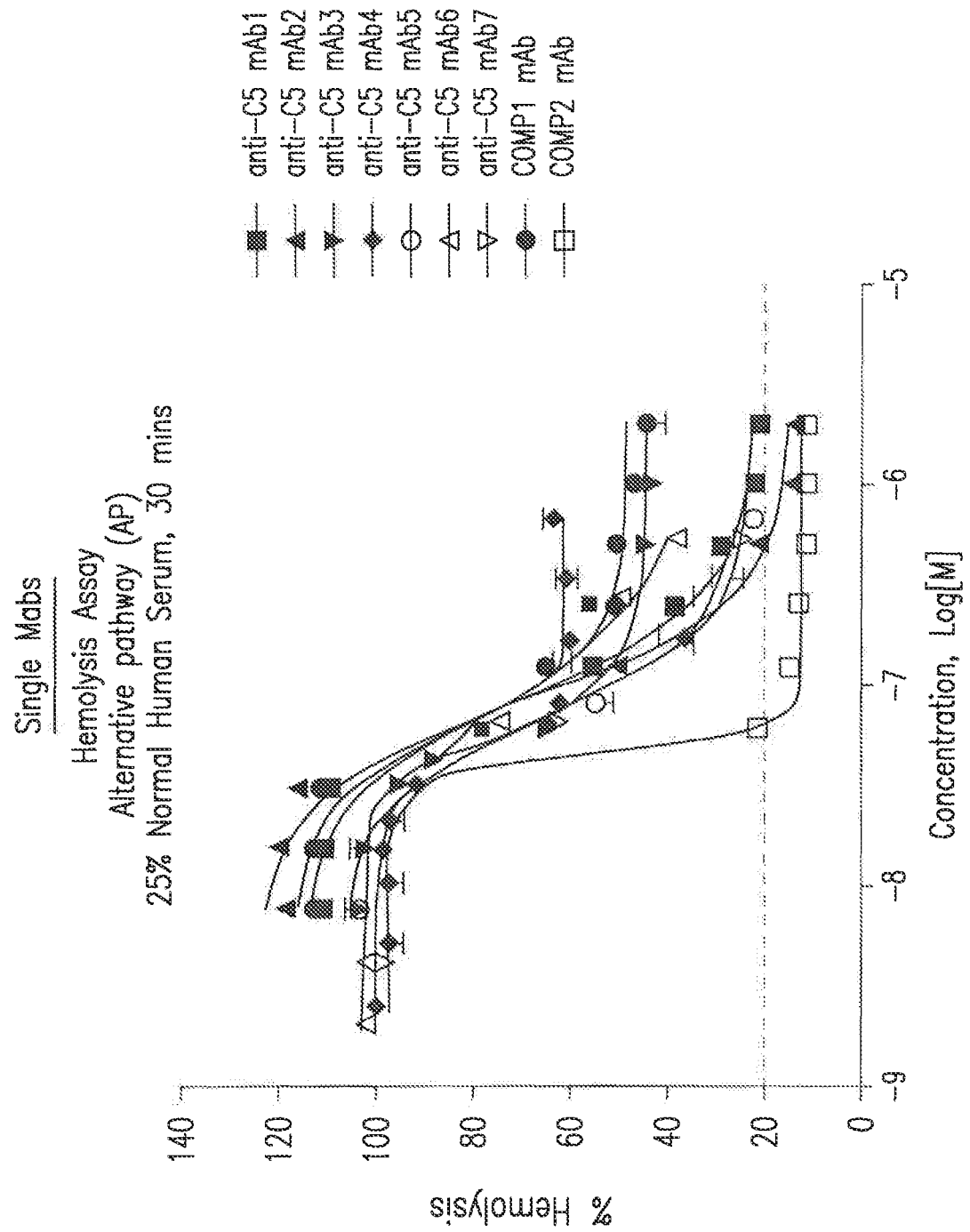

Anti-Protein Z mAb1 (lead anti-Protein Z mAb) in combination with COMP1 mAb or other Protein Z mAbs completely blocks hemolysis of rabbit RBCs via alternative pathway activation (FIG. 6B, Table 8), compared to monotherapies which do not completely block hemolysis (FIG. 6A, Table 7). Because all of the anti-Protein Z mAb1:anti-Protein Z mAb combinations completely blocked hemolysis of rabbit RBC, it was of importance: to determine if there are differences in complex formation, such as size, shape and orientation which can provide insight into the pharmacokinetics (PK) of a mAb during drug development, such as immunogenicity anchor target-mediated clearance.

TABLE 7

Effect of anti-Protein Z antibodies on rabbit RBC hemolysis.

| ABPID | AP, IC50 [M] | AP, IC80 [M] | % Max Inh. of Lysis |
|---|---|---|---|
| Anti-Protein Z mAb1 | 8.896e−008 | 1.970e−007 | 81.25 |
| Anti-Protein Z mAb2 | 8.366e−008 | 1.813e−007 | 88.66 |
| Anti-Protein Z mAb3 | 5.252e−008 | 9.390e−008 | 59.24 |
| Anti-Protein Z mAb4 | 4.942e−008 | 5.963e−008 | 38.63 |
| Anti-Protein Z mAb5 | 7.419e−008 | 1.467e−007 | 77.83 |
| Anti-Protein Z mAb6 | 9.346e−008 | 2.260e−007 | 62.80 |
| Anti-Protein Z mAb7 | 7.424e−008 | 1.414e−007 | 76.21 |
| COMP1 mAb | 8.291e−008 | 1.185e−007 | 61.14 |
| COMP2 mAb | 4.568e−008 | 5.600e−008 | 88.83 |

TABLE 8

Effect of anti-Protein Z antibody combinations on rabbit RBC hemolysis.

| ABPID | AP, IC50 [M] | AP, IC80 [M] | % Max Inh. of Lysis |
|---|---|---|---|
| Anti-Protein Z mAb1 + Anti-Protein Z mAb2 | 7.182e−008 | 7.528e−008 | 97.59 |
| Anti-Protein Z mAb1 + Anti-Protein Z mAb3 | 7.709e−008 | 8.749e−008 | 98.11 |
| Anti-Protein Z mAb1 + Anti-Protein Z mAb4 | 9.751e−008 | 1.064e−007 | 98.16 |
| Anti-Protein Z mAb1 + Anti-Protein Z mAb5 | 9.571e−008 | 1.051e−007 | 98.10 |
| Anti-Protein Z mAb1 + Anti-Protein Z mAb6 | 7.737e−008 | 8.461e−008 | 97.29 |
| Anti-Protein Z mAb1 + Anti-Protein Z mAb7 | 8.353e−008 | 9.432e−008 | 98.14 |
| Anti-Protein Z mAb1 COMP1 mAb | 7.372e−008 | 7.776e−008 | 98.26 |
| Anti-Protein Z mAb1 + COMP2 mAb | 7.306e−008 | 8.017e−008 | 98.07 |

Figure 7:
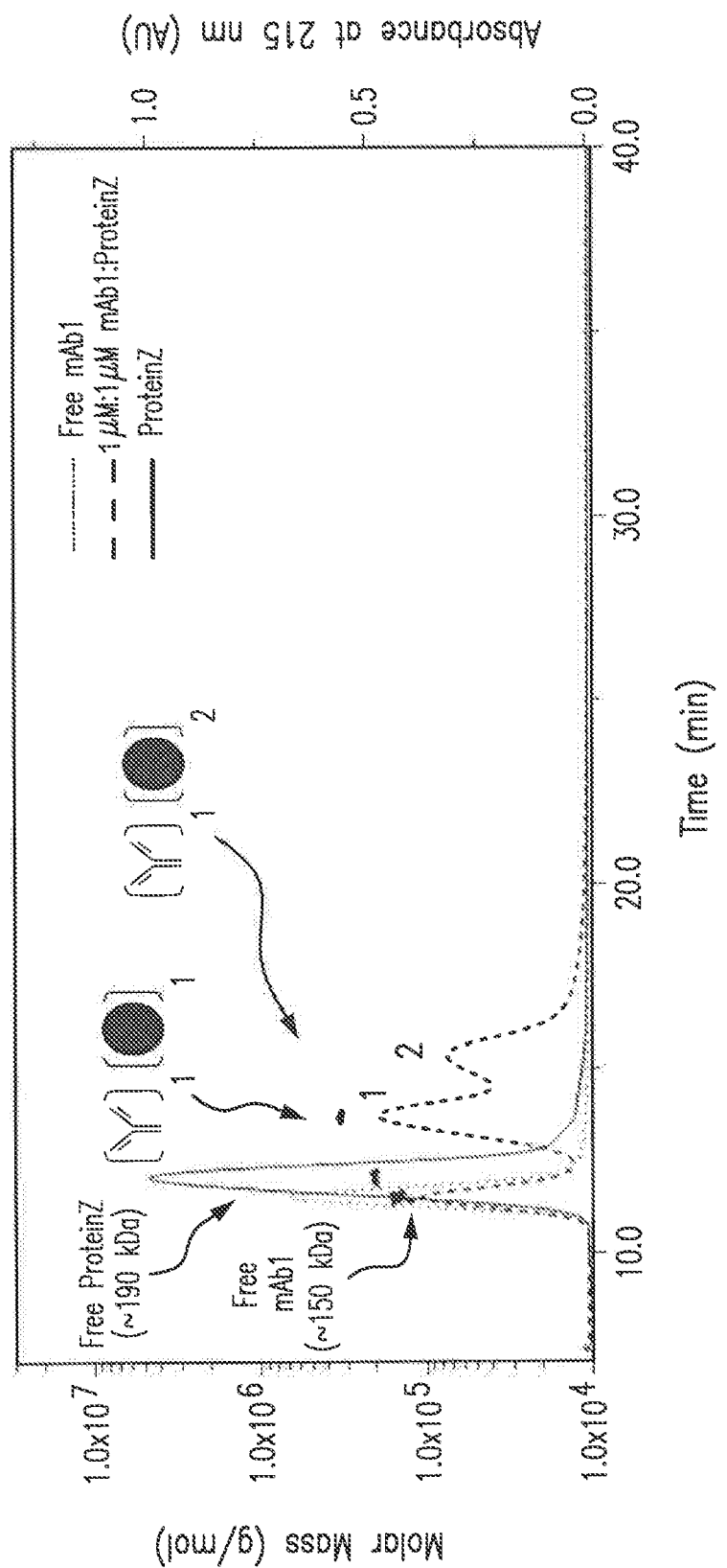
FIG. 7 is a fractogram from A4F-MALLS analysis of Free anti-Protein Z mAb1, Protein Z, and 1 µM:1 µM combination of anti-Protein Z mAb1 and Protein Z. The X axis represents elution time (minutes). The left Y axis represents molar mass (g/mol) and the right Y axis represents absorbance at 215 nm (AU).

In the absence of secondary mAbs, anti-Protein Z mAb1 formed canonical 1:1 and 1:2 complexes with Protein Z when mixed in equimolar amounts (FIG. 7, Table 9).

TABLE 9

Approximate molar mass and retention time for mAb:Protein Z complexes.

| | | Peak 1 [Intact Antibody]$_1$:[ProteinZ]$_1$ Complex | | Peak 2 [Intact Antibody]$_1$:[ProteinZ]$_2$ Complex | |
|---|---|---|---|---|---|
| Sample | Molar Ratio (mol:mol) | $R_t$, min | $M_w$, kDa | $R_t$, min | $M_w$, kDa |
| mAb1:ProteinZ | 1:1 | 13.7 | 341.1 | 15.3 | 498.7 |

Figure 8:
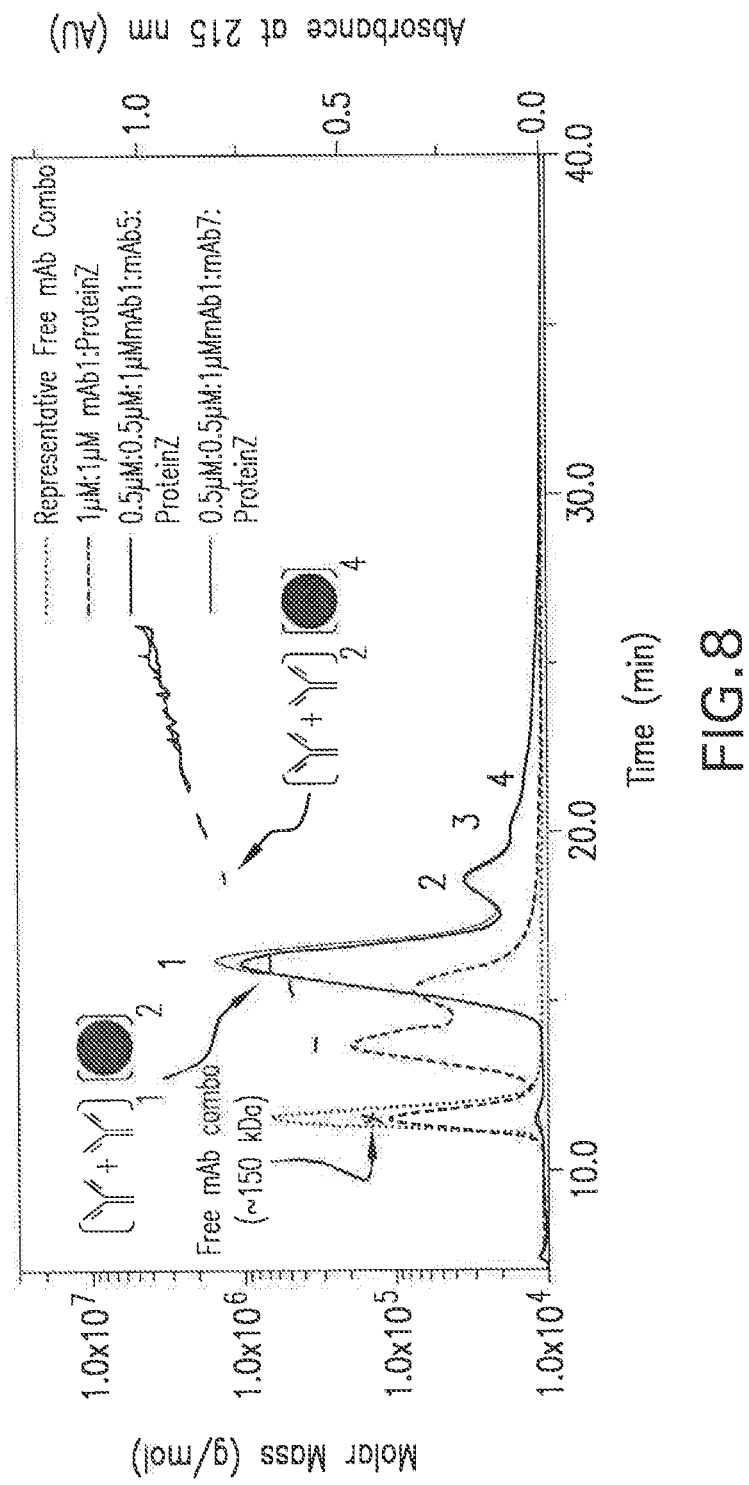
FIG. 8 is a fractogram from A4F-MALLS analysis of Free mAb, 1 µM:1 µM combination of anti-Protein Z mAb1 and Protein Z, 0.5 µM:1 µM combination of anti-Protein Z mAb1, anti-Protein Z mAb5, and Protein Z, and 0.5 µM:0.5 µM:1 µM combination of anti-Protein Z mAb1, anti-Protein Z mAb7, and Protein Z. The X axis represents elution time (minutes). The left Y axis represents molar mass (g/Mol) and the right Y axis represents absorbance at 215 nm (AU).
Figure 9:
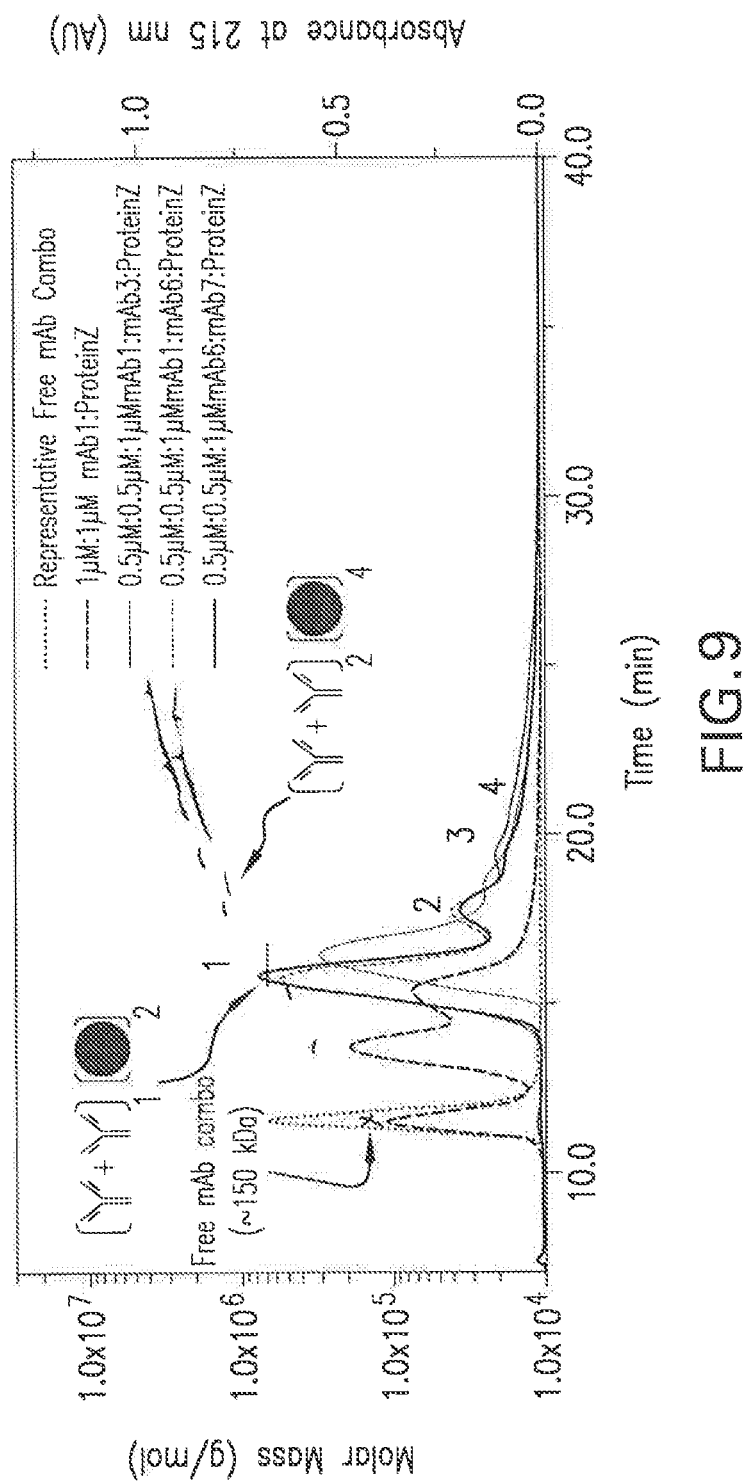
FIG. 9 is a fractogram from A4F-MALLS analysis of Free mAb combo, 1 µM:1 µM combination of anti-Protein Z mAb1 and Protein Z, 0.5 µM:0.5 µM:1 µM combination of anti-Protein Z mAb1, anti-Protein Z mAb3 combo, and Protein Z, and 0.5 µM:0.5 µM:1 µM combination of anti-Protein Z mAb1, anti-Protein Z mAb6 combo, and Protein Z, and 0.5 µM:0.5 µM:1 µM combination of anti-Protein Z mAb1, anti-Protein Z mAb6/anti-Protein Z mAb7, and Protein Z. The X axis represents elution time (minutes). The left Y axis represents molar mass (g/mol) and the right Y axis represents absorbance at 215 nm (AU).

$R_t$: Retention Time;
$M_w$: weight average molar mass;
min: minutes;
kDa: kiloDaltons;

Most secondary mAb combinations with anti-Protein Z mAb1 favored smaller, well defined complexes consistent with a heteromeric 2:2 mAb:Protein Z complex (FIGS. 8 and 9 and Tables 10-12).

TABLE 10

Theoretical molar mass of mAb:Protein Z complex.

| mAb:Protein Z Complex | Theoretical Molar Mass (KDa) |
|---|---|
| 1:0 | 150 |
| 0:1 | 195 |
| 1:1 | 345 |
| 2:1 | 495 |
| 1:2 | 540 |
| 2:2 | 690 |
| 3:2 | 840 |
| 2:3 | 885 |
| 4:4 | 1380 |
| 6:6 | 2070 |

TABLE 11

Approximate molar mass and retention time for mAb:Protein Z complexes.

| Sample | Molar Ratio (mol:mol) | Peak 1 [Intact Antibody]$_2$: [ProteinZ]$_2$ Complex | | Peak 2 [Intact Antibody]$_4$: [ProteinZ]$_4$ Complex | | Peak 3 [Intact Antibody]$_6$: [ProteinZ]$_6$ Complex | | Peak 4 Higher Order Complexes | |
|---|---|---|---|---|---|---|---|---|---|
| | | $R_t$, min | $M_w$, kDa | $R_t$, min | $M_w$, kDa | $R_t$, min | $M_w$, kDa | $R_t$, min | $M_w$, kDa |
| mAb1:mAb5:ProteinZ | 0.5:0.5:1 | 16.0 | 684.4 | 18.5 | 1342.4 | 20.1 | 1876.0 | 21.5 | ~2250-3560 |
| mAb1:mAb7:ProteinZ | 0.5:0.5:1 | 16.1 | 687.7 | 18.5 | 1327.4 | 20.1 | 1865.6 | 21.5 | ~2380-4250 |

$R_t$: Retention Time;
$M_w$: weight average molar mass;
min: minutes;
kDa: kiloDaltons;

TABLE 12

Approximate molar mass and retention time for mAb:Protein Z complexes.

| Sample | Molar Ratio (mol:mol) | Peak 1 [Intact Antibody]$_2$: [ProteinZ]$_2$ Complex | | Peak 2 [Intact Antibody]$_4$: [ProteinZ]$_4$ Complex | | Peak 3 [Intact Antibody]$_6$: [ProteinZ]$_6$ Complex | | Peak 4 Higher Order Complexes | |
|---|---|---|---|---|---|---|---|---|---|
| | | $R_t$, min | $M_w$, kDa | $R_t$, min | $M_w$, kDa | $R_t$, min | $M_w$, kDa | $R_t$, min | $M_w$, kDa |
| mAb1:mAb3:ProteinZ | 0.5:0.5:1 | 16.4 | 684.7 | 18.4 | 1261.8 | NA | NA | 20.2 | ~1700-2700 |
| mAb1:mAb6:ProteinZ | 0.5:0.5:1 | 15.7 | 685.9 | 17.7 | 1319.8 | 19.4 | 1849.8 | 20.6 | ~2300-3800 |
| mAb6:mAb7:ProteinZ | 0.5:0.5:1 | 15.8 | 687.7 | 17.8 | 1333.8 | 19.3 | 1871.6 | 20.6 | ~2300-3600 |

Figure 10:
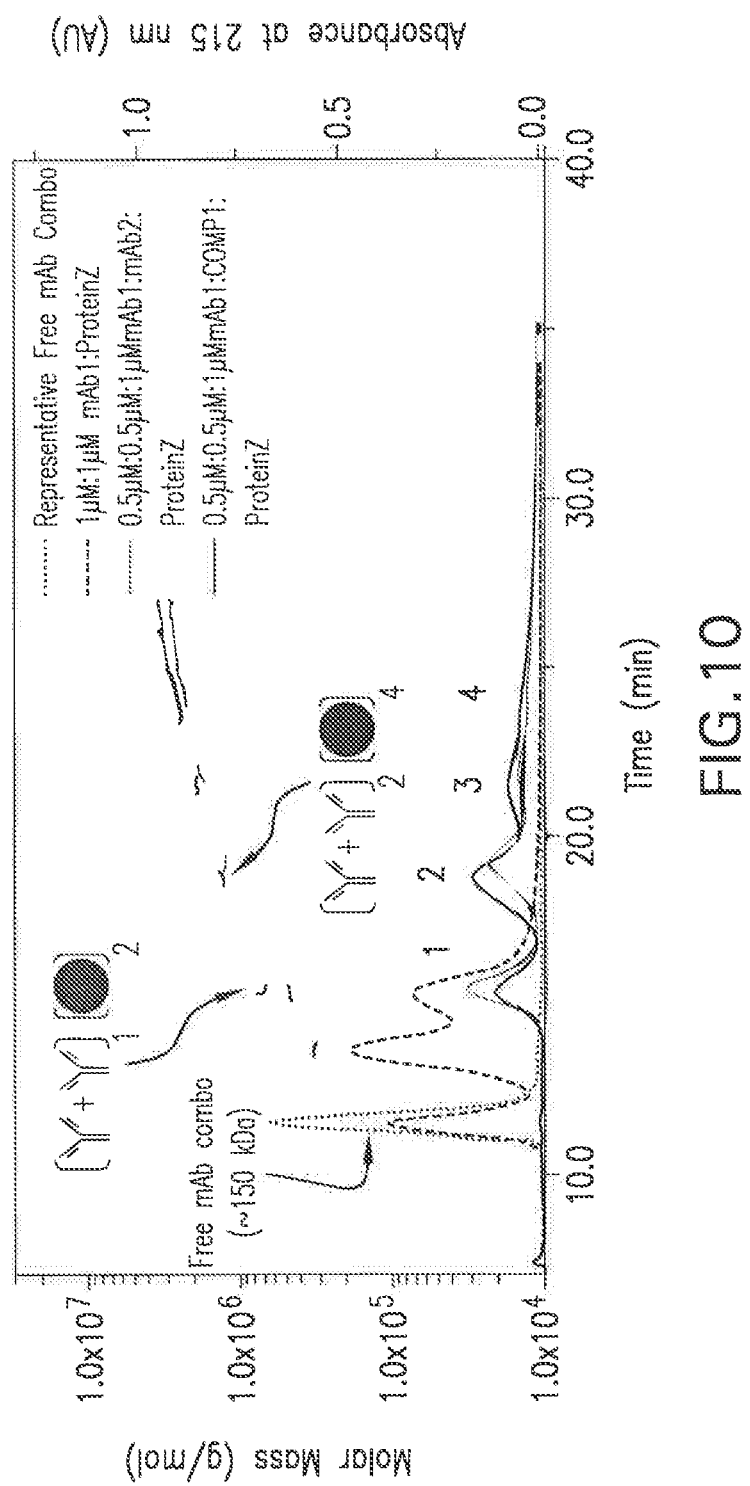
FIG. 10 is a factogram from A4F-MALLS analysis of free mAb combo, 1 µM:1 µM combination of anti-Protein Z mAb1 and Protein Z, 0.5 µM:0.5 µM:1 µM combination of anti-Protein Z mAb1, anti-Protein Z mAb2, and Protein Z, and 0.5 µM:0.5 µM:1 µM combination of anti-Protein Z mAb1, COMP1 mAb, and Protein Z. The X axis represents elution time (minutes). The left Y axis represents molar mass (g/mol) and the right Y axis represents absorbance at 215 nm (AU).

Although anti-Protein Z mAb1/anti-Protein Z mAb3 combination formed similar sized complexes with Protein Z, differences in elution time/profile suggested that complexes formed had differences in shape/orientation compared to other combinations (FIG. 9). Combinations of anti-Protein Z mAb1 with anti-Protein Z mAb2 and COMP1 mAb favored larger, more heterogeneous complexes with Protein Z indicative of "paper-dolling" (FIG. 10, Table 13).

TABLE 13

Approximate molar mass and retention time for mAb:Protein Z complexes.

| | | Peak 1 [Intact Antibody]$_2$: [ProteinZ]$_2$ Complex | | Peak 2 [Intact Antibody]$_4$: [ProteinZ]$_4$ Complex | | Peak 3 [Intact Antibody]$_6$: [ProteinZ]$_6$ Complex | | Peak 4 Higher Order Complexes | |
|---|---|---|---|---|---|---|---|---|---|
| Sample | Molar Ratio (mol:mol) | $R_t$, min | $M_w$, kDa | $R_t$, min | $M_w$, kDa | $R_t$, min | $M_w$, kDa | $R_t$, min | $M_w$, kDa |
| mAb1:mAb2:ProteinZ | 0.5:0.5:1 | 15.5 | 664.8 | 19.2 | 1304.3 | 21.9 | 1901.1 | 23.6 | ~2300-4100 |
| mAb1:COMP1:ProteinZ | 0.5:0.5:1 | 15.4 | 713.7 | 18.8 | 1346.1 | 21.5 | 2001.9 | 24.2 | ~2500-5000 |

Figure 11:
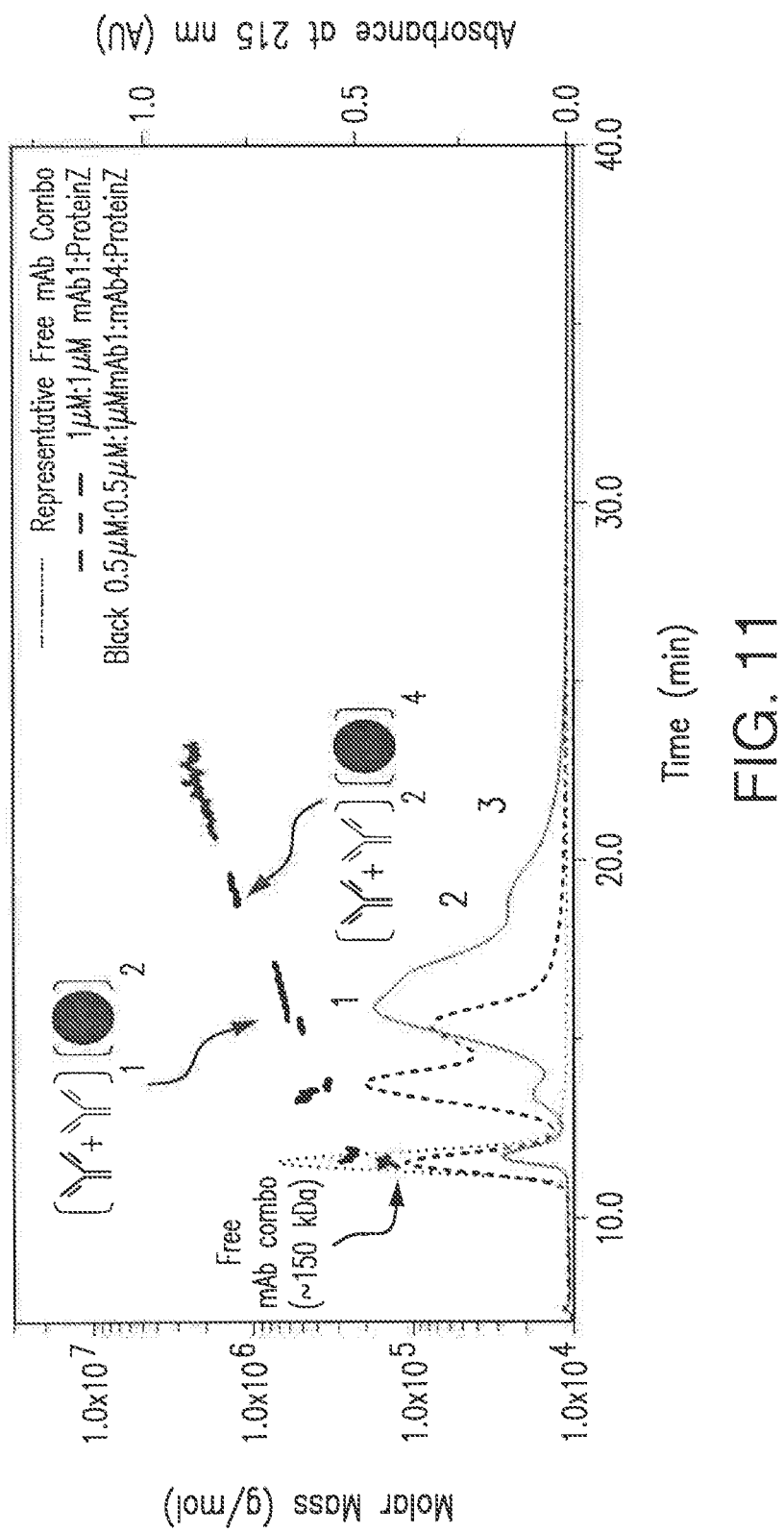
FIG. 11 is a fractogram from A4F-MALLS analysis of Free mAb combo, 1 µM:1 µM combination of anti-Protein Z mAb1 and Protein Z, 0.5 µM:0.5 µM:1 µM combination of anti-Protein Z mAb1, anti-Protein Z mAb4, and Protein Z. The X axis represents elution time (minutes). The left Y axis represents molar mass (g/mol) and the right Y axis represents absorbance at 215 nm (AU).

$R_t$: Retention Time;
$M_w$: weight average molar mass;
min: minutes;
kDa: kiloDaltons;

Anti-Protein Z mAb4 combination with anti-Protein Z mAb1 displayed a reduced tendency to form heteromeric complexes with Protein Z (FIG. 11, Table 14). Presence of free mAb and 1:1 mAb:Protein Z species indicated incomplete formation of heteromeric complexes with Protein Z. Mixtures of homomeric and heteromeric complexes with Protein Z were also evident.

TABLE 14

Approximate molar mass and retention time for mAb:Protein Z complexes.

| | | Peak 1 [Intact Antibody]$_2$: [ProteinZ]$_2$ Complex | | Peak 2 [Intact Antibody]$_4$: [ProteinZ]$_4$ Complex | | Peak 3 Higher Order Complexes | |
|---|---|---|---|---|---|---|---|
| Sample | Molar Ratio (mol:mol) | $R_t$, min | $M_w$, kDa | $R_t$, min | $M_w$, kDa | $R_t$, min | $M_w$, kDa |
| mAb1:mAb4:ProteinZ | 0.5:0.5:1 | 15.9 | 649.6 | 19.1 | 1288.2 | 20.6 | ~1700-2300 |

$R_t$: Retention Time;
$M_w$: weight average molar mass;
min: minutes;
kDa: kiloDaltons

Example 4: Order of Addition Does Not Significantly Impact the Molar Mass and Distribution of Complexes Formed Between Anti-Protein Z mAb1, COMP1 mAb, and Protein Z Methods To determine whether order of addition impacts complex formation, equimolar combinations of COMP1 mAb and Protein Z were prepared in 1×DPBS, pH 7.4 to yield a molar ratio of 1 µM COMP1 mAb:1 µM Protein Z and allowed to incubate at ambient temperature for 1 hr. Following incubation, varying amounts of Anti-Protein Z mAb1 was added to the pre-formed COMP1 mAb:Protein Z complexes and diluted in 1×DPBS, pH 7.4 to yield the following molar ratios: 0.3 µM Anti-Protein Z mAb1:1 µM COMP1 mAb: 1 µM Protein Z, 1 µM Anti-Protein Z mAb: 1 µM COMP1 mAb: 1 µM Protein Z, and 3 µM Anti-Protein Z mAb1: 1 µM COMP1 mAb: 1 µM Protein Z, and incubated for an additional hour prior to injection onto the instrument. The A4F MALLS analysis methods of Example 3 were followed.

Results

Figure 12A:
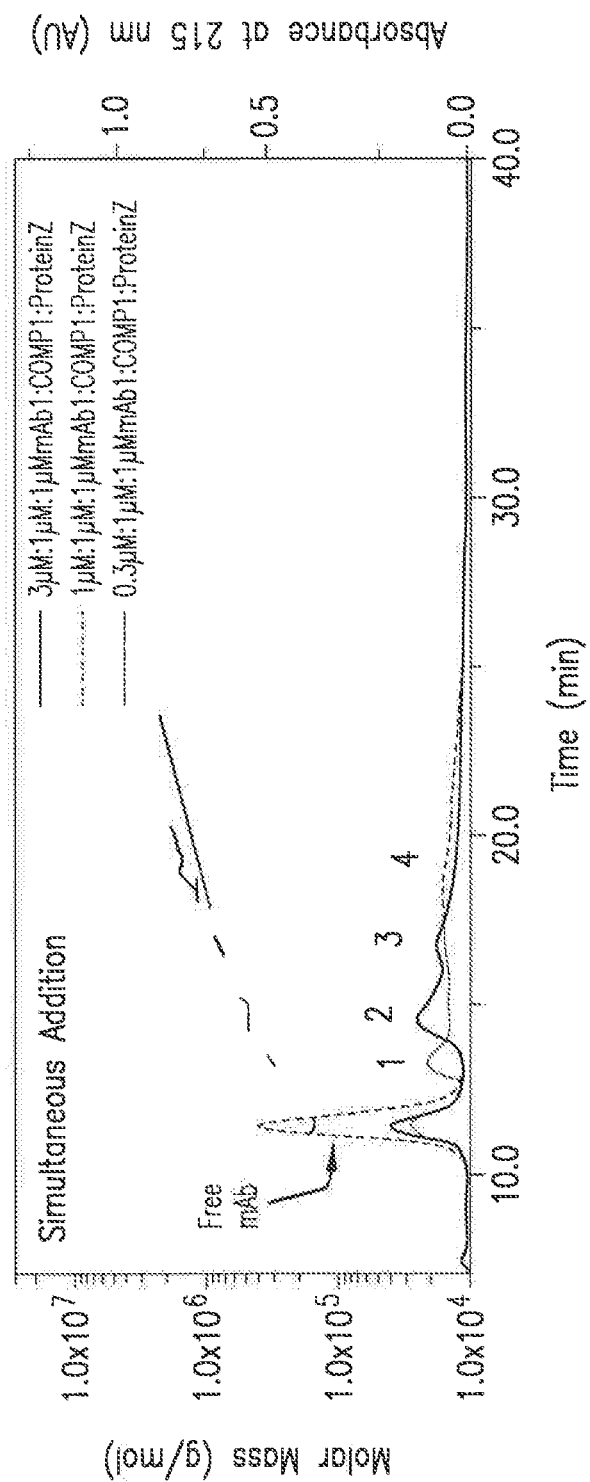
FIGS. 12A and 12B are fractograms from A4F-MALLS analysis of simultaneous addition (FIG. 12A) or sequential addition (FIG. 12B) of 0.3 µM:1 µM:1 µM anti-Protein Z mAb1:COMP1 mAb: Protein Z, 1 µM:1 µM:1 µM anti-Protein Z mAb1: COMP mAb:Protein Z, and 3 µM:1 µM:1 µM anti-Protein Z mAb1:COMP mAb:Protein Z. The X axis represents elution time (minutes). The left Y axis represents molar mass (g/mol) and the right Y axis represents absorbance at 215 nm (AU).
Figure 12B:
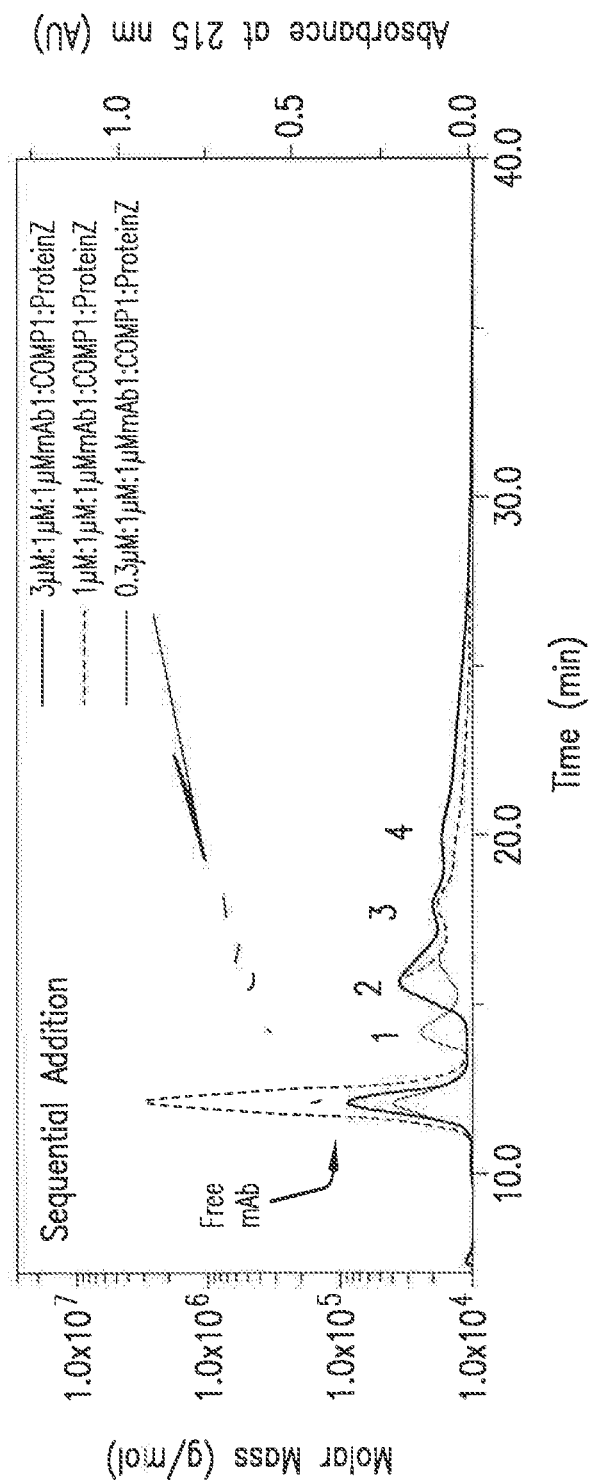

Similar complexes, with respect to molar mass and distribution, were formed between anti-Protein Z mAb1 COMP1 mAb, and Protein Z regardless of whether anti-Protein Z mAb1 was added simultaneously (FIG. 12A, Table 15) or sequentially (FIG. 12B, Table 15) to the other components. The slight shift in elution time observed between the two datasets is indicative of the variability inherent to the method and is not considered unusual.

TABLE 15

Approximate molar mass and retention time for mAb:Protein Z complexes.

| | | Peak 1 [Intact Antibody]$_1$: [ProteinZ]$_1$ Complex | | Peak 2 [Intact Antibody]$_1$: [ProteinZ]$_2$ Complex | | Peak 3 [Intact Antibody]$_{2-3}$: [ProteinZ]$_{2-3}$ Complex | | Peak 4 Higher Order Complexes | |
|---|---|---|---|---|---|---|---|---|---|
| Sample | mAb1:COMP1:ProteinZ Molar Ratio (mol:mol) | $R_t$, min | $M_w$, kDa | $R_t$, min | $M_w$, kDa | $R_t$, min | $M_w$, kDa | $R_t$, min | $M_w$, kDa |
| Simultaneous Addition | 3:1:1 | NA | NA | 14.5 | 536.6 | 16.7 | 888.6 | 18.0 | ~1200-1950 |
| | 1:1:1 | NA | NA | 14.6 | 522.7 | 16.7 | 793.1 | 18.6 | ~1400-2300 |
| | 0.3:1:1 | 13.3 | 343.7 | 15.0 | 540.9 | 16.6 | 750.3 | 18.4 | ~1000-1800 |

TABLE 15-continued

Approximate molar mass and retention time for mAb:Protein Z complexes.

| Sample | mAb1:COMP1:ProteinZ Molar Ratio (mol:mol) | Peak 1 [Intact Antibody]$_1$: [ProteinZ]$_1$ Complex | | Peak 2 [Intact Antibody]$_1$: [ProteinZ]$_2$ Complex | | Peak 3 [Intact Antibody]$_{2-3}$: [ProteinZ]$_{2-3}$ Complex | | Peak 4 Higher Order Complexes | |
|---|---|---|---|---|---|---|---|---|---|
| | | $R_t$, min | $M_w$, kDa | $R_t$, min | $M_w$, kDa | $R_t$, min | $M_w$, kDa | $R_t$, min | $M_w$, kDa |
| Sequential Addition | 3:1:1 | NA | NA | 15.6 | 500.1 | 18.0 | 816.9 | 20.0 | ~1200-1800 |
| | 1:1:1 | NA | NA | 15.7 | 496.4 | 18.0 | 806.2 | 20.0 | ~1500-2400 |
| | 0.3:1:1 | 14.2 | 379.8 | 16.4 | 662.7 | 17.9 | 817.8 | 19.9 | ~1500-2600 |

Example 5 Anti-Protein W Complexes

Methods

A4F-MALLS Mobile Phase Buffer

The mobile phase buffer (10 mM sodium phosphate, 500 mM sodium chloride, pH 7.0±0.1) was prepared by combining 1.4 g sodium phosphate monobasic monohydrate, 10.7 g sodium phosphate dibasic heptahydrate, and 500 mL 5 M sodium chloride; the solution was then brought to a volume to 5.0 L with HPLC grade water. The final measured pH of the buffer was 7.0. The mobile phase buffer was filtered (0.2 µm) before use.

A4F MALLS Analysis

The A4F-MALLS system was composed of an Eclipse™ 3+ A4F Separation System coupled to an Agilent 1200 Series HPLC system equipped with a ultraviolet (UV) diode array detector, Wyatt Technology Dawn HELEOS® II laser light scattering instrument (LS), and an Optilab® T-rEX differential refractometer (RI) detector. The detectors were connected in series in the following order: UV-LS-RI. LS and RI detectors were calibrated according to instructions provided by Wyatt Technology.

Defined amounts of anti-Protein W mAb were each combined with Protein W and diluted in 1×DPBS, pH 7.4 to yield the equimolar ratio: 1 µM anti-Protein W mAb: 1 µM Protein W. All samples were incubated at ambient temperature for 2 hours and maintained unfiltered at 4° C. prior to injection into an Eclipse™ short channel fitted with a W350 spacer foil (350 µm spacer thickness, 2.2 cm spacer width) and using a 10 kDa MWCO regenerated cellulose membrane. The channel was pre-equilibrated with the mobile phase buffer (10 mM sodium phosphate, 500 mM sodium chloride, pH 7.0±0.1), prior to the injection of each sample. Bovine serum albumin (BSA; 2 mg/mL; 10 µg sample load) was injected separately and included as a system suitability control.

The fractionation method consisted of four steps: injection, focusing, elution, and a channel "wash-out" step. The A4F-MALLS mobile phase buffer (10 mM sodium phosphate, 500 mM sodium chloride, pH 7.0±0.1) was used throughout the fractionation method. Each sample (7 µg) was injected at a flow rate of 0.2 mL/min for 1 min and subsequently focused for 3 min with a focus flow rate of 1.0 mL/min. The sample was eluted with a channel flow rate of 1.0 mL/min with the linear gradient cross flow from 3.0 mL/min to 0 mL/rain over 25 min. Finally, the cross flow was held at 0 mL/min for an additional 5 min to wash out the channel. BSA was fractionated using the same parameter settings.

Results:

A4F-MALLS was used to assess the relative size distribution of complexes formed between Protein W, a dimeric, multi-domain ligand, and several anti-Protein W antibodies that specifically bind to different domains within the ligand. The theoretical molar mass and predicted stoichiometry of potential antibody complexes with Protein W are provided in Table 16.

TABLE 16

Theoretical Molar Mass of mAb:Protein W Complexes.

| mAb:ProteinW Complex | Theoretical Molar Mass (kDa) |
|---|---|
| 1:0 | 146 |
| 0:1 | 146 |
| 1:1 | 292 |
| 1:2[1] | 438 |
| 2:2 | 584 |
| 2:3[1] | 730 |
| 3:3 | 876 |
| 3:4[1] | 1022 |
| 4:4 | 1168 |

[1]Unequal ratios (such as 1:2 and 2:1 cannot be differentiated, because they will have same MW.

Figure 13:
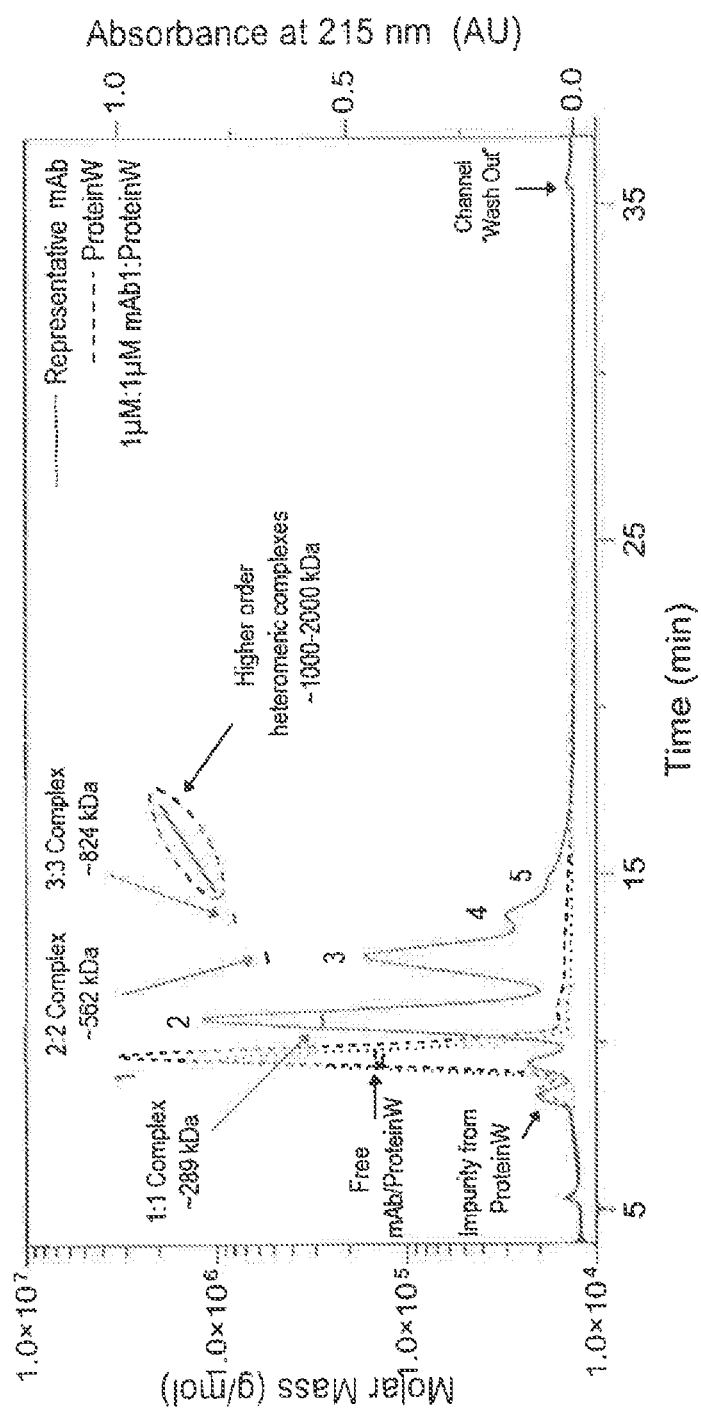
FIG. 13 is a fractogram from A4F-MALLS analysis of a representative mAb, Protein W, and combinations of mAb and Protein W at ratios of 1 µM:1 µM. The X axis represents elution time (minutes). The left Y axis represents molar mass (g/mol) and the right Y axis represents absorbance at 215 nm (AU).

Overall, out of the panel of mAbs, mAb1 targeting Domain A formed the highest proportion of lower-order complexes with the predominant species representing a discrete 1:1 and 2:2 complex with Protein W when combined at equimolar ratios (Peak 2, ~289 kDa; and peak 3, ~562 kDa, FIG. 13, Table 17).

TABLE 17

Molar Masses and Retention Time of Human Protein W Complexes with mAb1 Targeting Domain A.

| Sample | Molar Ratio (mol:mol) | Peak 1 Free mAb/ProteinW | | Peak 2 [mAb]₁:[ProteinW]₁ Complex | | Peak 3 [mAb]₂:[ProteinW]₂ Complex | | Peak 4 [mAb]₃:[ProteinW]₃ Complex | | Peak 5 Higher Order Heteromeric Complexes | |
|---|---|---|---|---|---|---|---|---|---|---|---|
| | | $R_t$, min | $M_w$, kDa | $R_t$, min | $M_w$, kDa | $R_t$, min | $M_w$, kDa | $R_t$, min | $M_w$, kDa | $R_t$, min | $M_w$, kDa |
| ProteinW | — | 9.6 | 146.6 | ND | ND | ND | ND | ND | ND | ND | ND |
| mAb1 | — | 9.5 | 145.1 | ND | ND | ND | ND | ND | ND | ND | ND |
| mAb1:ProteinW | 1:1 | 9.3 | 145.7 | 10.7 | 288.6 | 12.6 | 561.9 | 13.7 | 823.9 | 14.5 | ~1000-2000 |

$R_t$: Retention Time;
$M_w$: weight average molar mass;
NA: Not Applicable;
min: minutes;
kDa: kiloDaltons.

Figure 14:
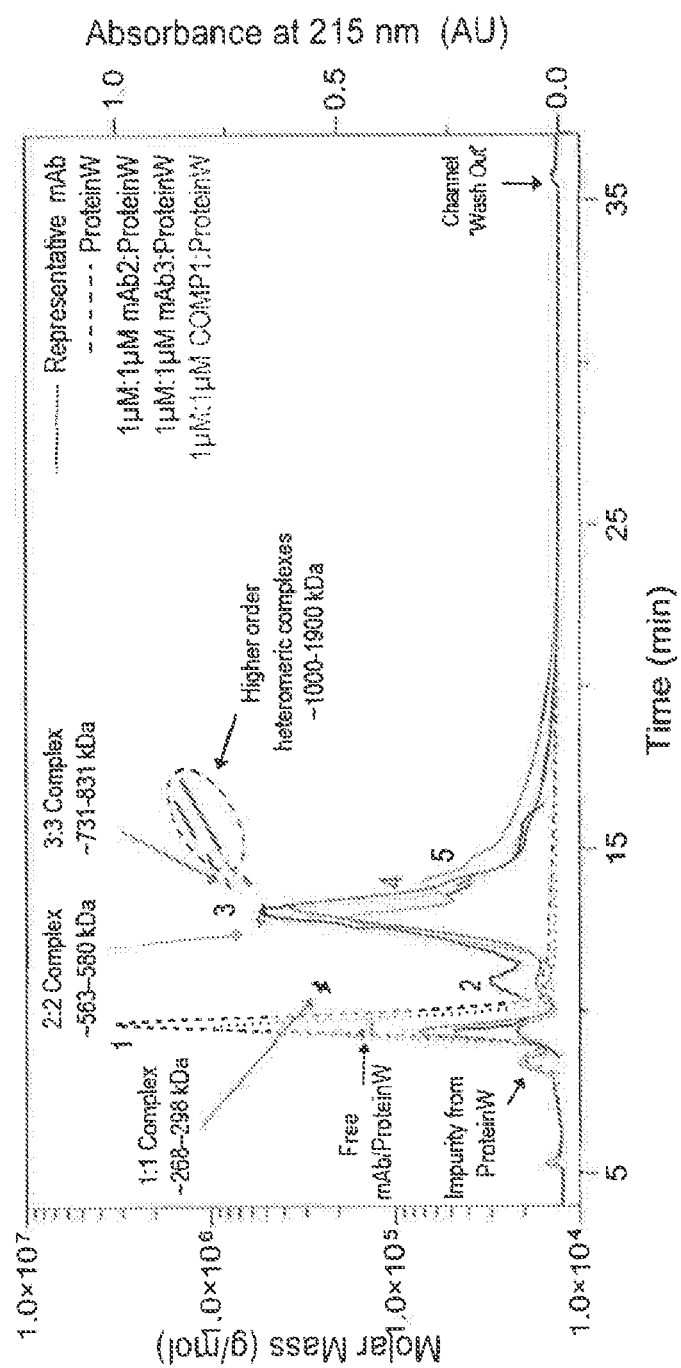
FIG. 14 is a fractogram from A4F-MALLS analysis of a representative mAb, Protein W, and combinations of mAb2 and Protein W, mAb3 and Protein W, and COMP1 and Protein W at ratios of 1 µM:1 µM. The X axis represents elution time (minutes). The left Y axis represents molar mass (g/mol) and the right Y axis represents absorbance at 215 nm (AU).
Figure 15:
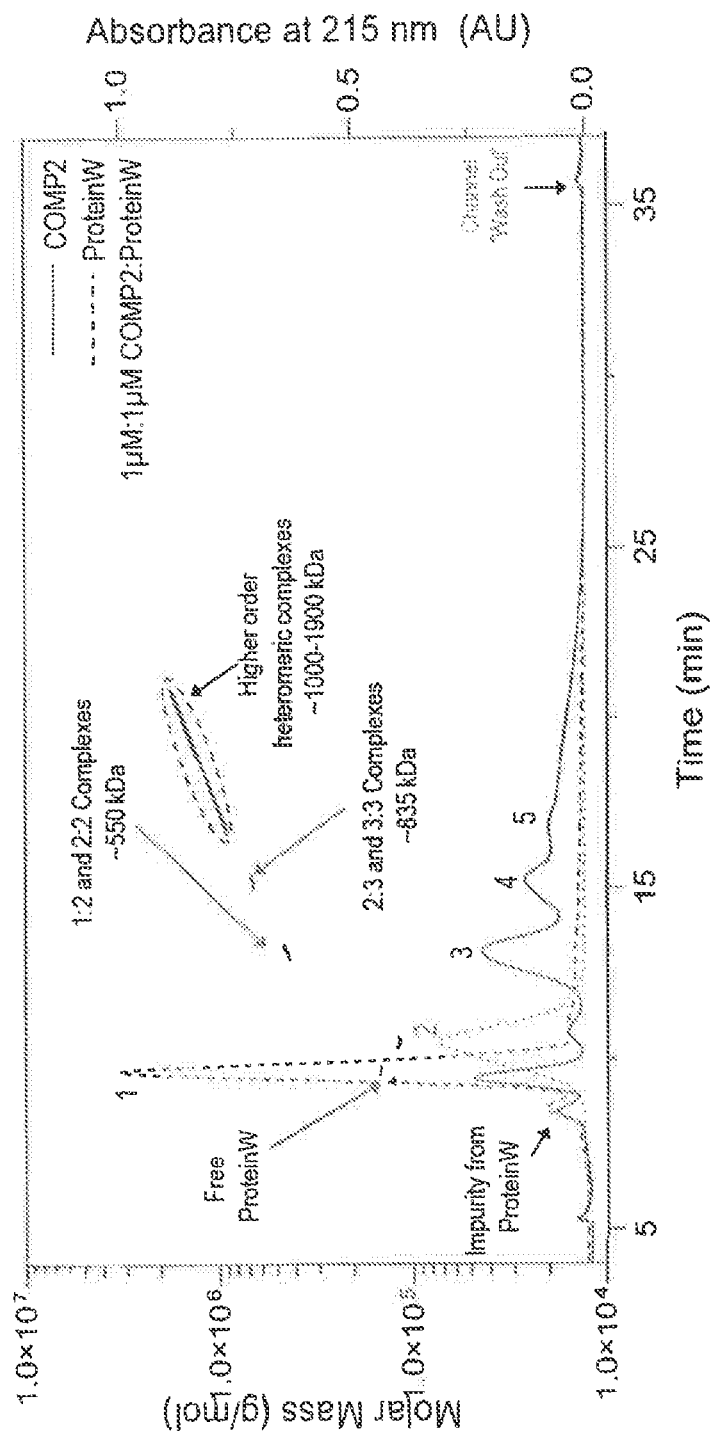
FIG. 15 is a fractogram from A4F-MALLS analysis of COMP2, Protein W, and combinations of COMP2 and Protein W at ratios of 1 μM:1 μM. The X axis represents elution time (minutes). The left Y axis represents molar mass (g/mol) and the right Y axis represents absorbance at 215 nm (AU).

Each of the mAbs targeting DomainB (mAb2, mAb3 and COMP1) predominantly formed a discrete 2:2 complex with ProteinW (Peak 3, ~563-580 kDa, FIG. 14, Table 18) with mAb2 and COMP1 forming the most homogeneous distribution of complexes relative to other mAbs tested. While COMP2 targeting DomainA primarily favored a mixture of 1:2 and 2:2 complexes with Protein W (Peak 3, ~550 kDa, FIG. 15, Table 19), a moderate degree of large, heterogeneous complexes was also observed. This suggests that unlike mAb1, which also targeted DomainA, COMP2 binds to a unique epitope on ProteinW that allows for the formation of extended antibody-antigen lattices in a process termed "paper-dolling". In this sample, a distinct peak (Peak 4) having a molar mass of approximately 835 kDa was observed, followed by a series of broad, poorly-resolved species (peak 5) with a wide molar mass distribution ranging from ~1000-1900 kDa (FIG. 15, Table 19).

TABLE 18

Molar Masses and Retention Time of Human Protein W Complexes with mAbs targeting the Domain B.

| Sample | Molar Ratio (mol:mol) | Peak 1 Free mAb/ProteinW | | Peak 2 [mAb]₁:[ProteinW]₁ Complex | | Peak 3 [mAb]₂:[ProteinW]₂ Complex | | Peak 4 [mAb]₃:[ProteinW]₃ Complex | | Peak 5 Higher Order Heteromeric Complexes | |
|---|---|---|---|---|---|---|---|---|---|---|---|
| | | $R_t$, min | $M_w$, kDa | $R_t$, min | $M_w$, kDa | $R_t$, min | $M_w$, kDa | $R_t$, min | $M_w$, kDa | $R_t$, min | $M_w$, kDa |
| ProteinW | — | 9.6 | 146.6 | ND | ND | ND | ND | ND | ND | ND | ND |
| mAb2 | — | 9.6 | 152.1 | ND | ND | ND | ND | ND | ND | ND | ND |
| mAb2:ProteinW | 1:1 | 9.4 | 144.4 | 10.9 | 282.5 | 13.2 | 574.2 | 13.9 | 731.3 | 15.4 | ~1000-1900 |
| mAb3:ProteinW | 1:1 | 9.3 | 144.1 | 10.7 | 267.8 | 12.9 | 562.5 | 14.0 | 830.5 | 14.6 | ~1000-1900 |
| COMP1:ProteinW | 1:1 | 9.4 | 143.1 | 10.8 | 298.3 | 13.0 | 580.1 | 13.9 | 764.7 | 15.0 | ~1000-1900 |

$R_t$: Retention Time;
$M_w$: weight average molar mass;
NA: Not Applicable:
min: minutes;
kDa: kiloDaltons.

TABLE 19

Molar Masses and Retention Time of Human Protein W Complexes with COMP2 targeting Domain A.

| Sample | Molar Ratio (mol:mol) | Peak 1 Free ProteinW | | Peak 2 Free mAb | | Peak 3 [mAb]$_{1-2}$: [ProteinW]$_2$ Complex | | Peak 4 [mAb]$_{2-3}$: [ProteinW]$_3$ Complex | | Peak 5 Higher Order Heteromeric Complexes | |
|---|---|---|---|---|---|---|---|---|---|---|---|
| | | $R_t$, min | $M_w$, kDa | $R_t$, min | $M_w$, kDa | $R_t$, min | $M_w$, kDa | $R_t$, min | $M_w$, kDa | $R_t$, min | $M_w$, kDa |
| ProteinW | — | 9.6 | 146.6 | ND | ND | ND | ND | ND | ND | ND | ND |
| COMP2 | — | 10.5 | 121.9 | ND | ND | ND | ND | ND | ND | ND | ND |
| COMP2:ProteinW | 1:1 | ND | ND | 9.4 | 147.1 | 13.1 | 550.2 | 15.2 | 835.1 | 16.9 | ~1000-1900 |

$R_t$: Retention Time;
$M_w$: weight average molar mass;
NA: Not Applicable;
min: minutes;
kDa: kiloDaltons.

Figure 16:
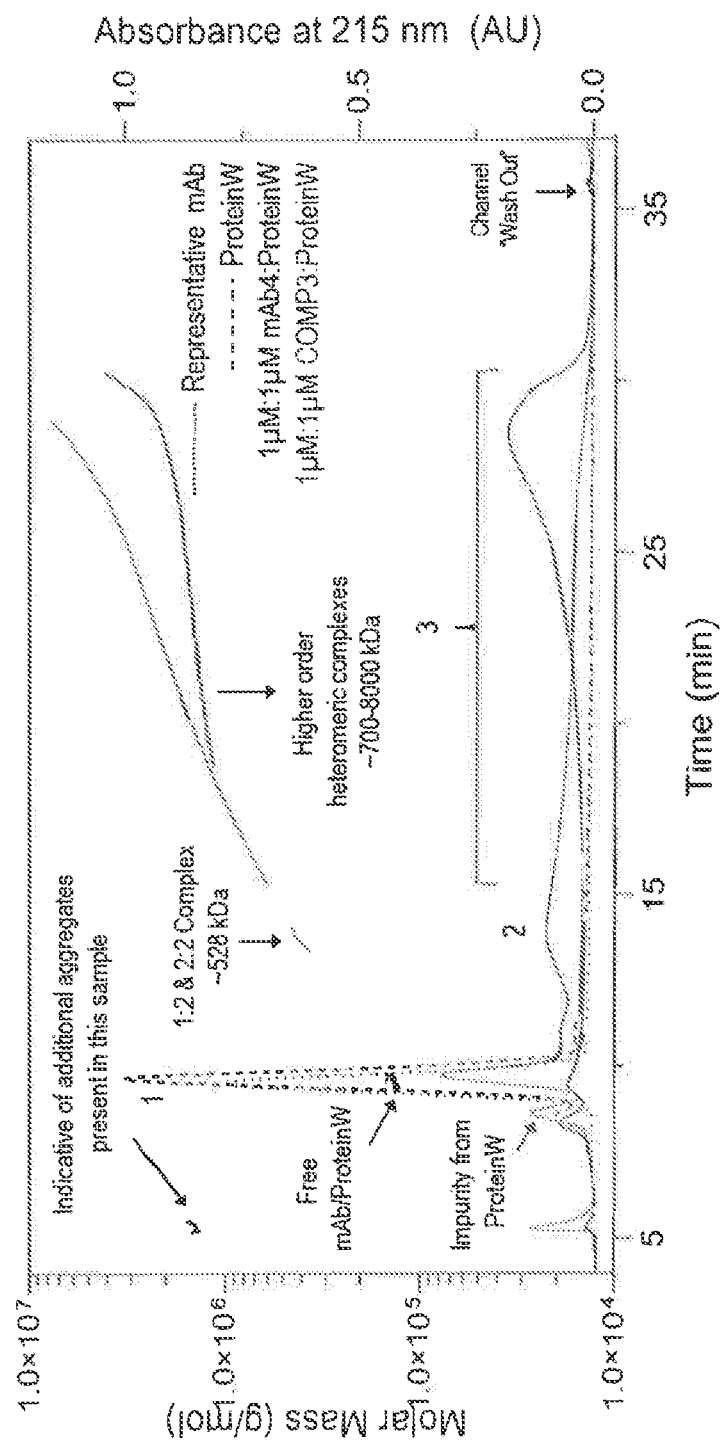
FIG. 16 is a fractogram from A4F-MALLS analysis of a representative mAb, Protein W, and combinations of mAb4 and Protein W, and COMP3 and Protein W at ratios of 1 μM:1 μM. The X axis represents elution time (minutes). The left Y axis represents molar mass (g/mol) and the right Y axis represents absorbance at 215 nm (AU).

Based on the calculated molar masses of the individual components, peak 4 likely represents complexes containing at least 3 molecules of mAb coordinating 2-3 molecules of Protein W, whereas peak 5 corresponds to a heterogeneous distribution of higher order heteromeric complexes composed of ≥3 molecules of mAb coordinating ≥4 molecules of Protein W (Table 18). In contrast, mAbs targeting Domain C (mAb4 and COMP3); formed a broad distribution of large, heterogeneous complexes (molar mass ranging from ~700-8000 kDa) with mAb4 displaying the most extensive "paper-dolling" amongst the panel of mAbs tested (FIG. 16, Table 20).

TABLE 20

Molar Masses and Retention Time of Human ProteinW Complexes with mAbs targeting Domain C.

| Sample | Molar Ratio (mol:mol) | Peak 1 Free mAb/ProteinW | | Peak 2 [mAb]$_{1-2}$: [ProteinW]$_2$ Complex | | Peak 3 Higher Order Heteromeric Complexes | |
|---|---|---|---|---|---|---|---|
| | | $R_t$, min | $M_w$, kDa | $R_t$, min | $M_w$, kDa | $R_t$, min | $M_w$, kDa |
| PorteinW | — | 9.6 | 146.6 | ND | ND | ND | ND |
| mAb4 | — | 9.5 | 148.3 | ND | ND | ND | ND |
| mAb4:ProteinW | 1:1 | 9.5 | 157.7 | ND | ND | 28.5 | 1400-4000 |
| COMP3:ProteinW | 1:1 | 9.7 | 161.3 | 13.9 | 528.4 | 14.6 | 700-8000 |

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method for assessing the stoichiometry and size distribution of heterogeneous protein complexes in a sample, wherein the method comprises the steps of:
fractionating the sample by asymmetrical flow field flow fractionation (A4F) using a perpendicularly-opposed cross-flow separation field that has a linear gradient cross flow, wherein the sample is eluted with a linear gradient cross flow from 3.0 mL/min to 0 mL/min;
determining the molar mass, stoichiometry, and size distribution of the heterogeneous protein complexes in the sample using Multi-Angle Laser Light Scattering (MALLS), wherein the heterogeneous protein complexes comprise heterogeneous protein:ligand complexes comprising more than one protein bound to the ligand; and
identifying the stoichiometry and size distribution of the heterogeneous protein:ligand complexes, wherein the protein in the heterogeneous protein ligand complexes is a monoclonal antibody or an antigen binding fragment thereof.

2. The method of claim 1, wherein the ligand is a soluble ligand.

3. The method of claim 1, wherein the monoclonal antibody is a bispecific antibody or an antigen binding fragment thereof.

4. The method of claim 1, wherein the monoclonal antibody and the antigen binding fragment thereof in the heterogeneous protein:ligand complexes is the same type of antibody.

5. The method of claim 1, wherein the heterogeneous protein:ligand complex is an antibody:ligand complex having a monoclonal antibody to ligand molar ratio of 2:1.

6. The method of claim 1, wherein the heterogeneous antibody ligand complex has a molecular weight of 700 kDa to 8000 kDa.

7. The method of claim 1, wherein the heterogeneous antibody:ligand complex has a molecular weight of 500 kDa to 4000 kDa.

8. The method of claim 1, wherein the A4F is performed with a channel with a W350 spacer foil having a thickness of 350 μm and a width of 2.2 cm.

9. The method of claim 1, wherein the A4F is performed with a channel with a W490 spacer foil having a thickness of 490 μm and a width of 2.2 cm.

10. The method according to claim 1, wherein the fractionating step comprises (i) injection of the sample into the sample inlet port of the A4F channel and (ii) then focus of the sample by allowing the carrier fluid to flow into the channel from an inlet port and an outlet port.

11. The method according to claim 10, wherein smaller protein:ligand complexes will elute before larger protein:ligand complexes.

12. The method according to claim 1, wherein the fractionating step comprises (i) injection of the sample into the sample inlet port of the A4F channel and (ii) then focus of the sample by allowing the carrier fluid to flow into the channel from an inlet port and an outlet port.

13. The method according to claim 12, wherein smaller protein:ligand complexes will elute before larger antibody:ligand complexes.

14. The method of claim 1, wherein the sample is eluted with a channel flow rate of 1.0 mL/min.

15. The method of claim 1, wherein the sample is eluted with a linear gradient cross flow from 1.2 mL/min to 0 mL/min.

16. The method of claim 1, wherein the sample is eluted with a linear gradient cross flow from 1.2 mL/min to 0 mL/min over 20 minutes.

17. The method of claim 1, wherein the sample is eluted with a linear gradient cross flow from 2.0 mL/min to 0 mL/min.

18. The method of claim 1, wherein the sample is eluted with a linear gradient cross flow from 2.0 mL/min to 0 mL/min over 45 minutes.

19. The method of claim 1, wherein the sample is eluted with a linear gradient cross flow from 3.0 mL/min to 0 mL/min over 25 minutes.

20. The method of claim 1, wherein the sample is eluted with a linear gradient cross flow from 3.0 mL/min to 0 mL/min over 45 minutes.

\* \* \* \* \*

UNITED STATES PATENT AND TRADEMARK OFFICE
CERTIFICATE OF CORRECTION

| | | |
|---|---|---|
| PATENT NO. | : 11,754,569 B2 | Page 1 of 1 |
| APPLICATION NO. | : 16/553312 | |
| DATED | : September 12, 2023 | |
| INVENTOR(S) | : Nina Liu et al. | |

It is certified that error appears in the above-identified patent and that said Letters Patent is hereby corrected as shown below:

In the Claims

Delete Column 32, Lines 20-32, and move the following to Claim 1, Column 32, above Line 48:
"fractionating the sample by asymmetrical flow field flow fractionation (A4F) using a perpendicularly-opposed cross-flow separation field that has a linear gradient cross flow, wherein the sample is eluted with a linear gradient cross flow from 3.0 mL/min to 0 mL/min;
determining the molar mass, stoichiometry, and size distribution of the heterogeneous protein complexes in the sample using Multi-Angle Laser Light Scattering (MALLS), wherein the heterogeneous protein complexes comprise heterogeneous protein:ligand complexes comprising more than one protein bound to the ligand; and"

At Column 32, Line 50, Claim 1, replace "protein ligand" with "protein:ligand"

Signed and Sealed this
Ninth Day of September, 2025

Coke Morgan Stewart
*Acting Director of the United States Patent and Trademark Office*